(12) United States Patent
Liu et al.

(10) Patent No.: US 11,897,960 B2
(45) Date of Patent: Feb. 13, 2024

(54) ANTI-IL-4R ANTIBODY AND USE THEREOF

(71) Applicants: Beijing Wisdomab Biotechnology Co., Ltd, Beijing (CN); Genrix (Shanghai) Biopharmaceutical Co. Ltd., Shanghai (CN); Chongqing Genrix Biopharmaceutical Co., Ltd., Chongqing (CN)

(72) Inventors: Zhigang Liu, Beijing (CN); Yulan Liu, Beijing (CN); Xiaobo Hao, Beijing (CN); Lei Jiang, Beijing (CN); Jingjing Guo, Beijing (CN)

(73) Assignees: Beijing Wisdomab Biotechnology Co., Ltd, Beijing (CN); Genrix (Shanghai) Biopharmaceutical Co. Ltd., Shanghai (CN); Chongqing Genrix Biopharmaceutical Co., Ltd., Chongqing (CN)

( * ) Notice: Subject to any disclaimer, the term of this patent is extended or adjusted under 35 U.S.C. 154(b) by 449 days.

(21) Appl. No.: 17/049,288

(22) PCT Filed: Aug. 13, 2018

(86) PCT No.: PCT/CN2018/100263
§ 371 (c)(1),
(2) Date: Oct. 20, 2020

(87) PCT Pub. No.: WO2019/200787
PCT Pub. Date: Oct. 24, 2019

(65) Prior Publication Data
US 2022/0081485 A1  Mar. 17, 2022

(30) Foreign Application Priority Data
Apr. 20, 2018 (CN) .................. 201810360234.5

(51) Int. Cl.
*C07K 16/28* (2006.01)
*A61K 39/00* (2006.01)

(52) U.S. Cl.
CPC ..... *C07K 16/2866* (2013.01); *A61K 2039/505* (2013.01); *C07K 2317/565* (2013.01)

(58) Field of Classification Search
CPC .......... C07K 16/2866; C07K 2317/565; A61K 2039/505
See application file for complete search history.

(56) References Cited

U.S. PATENT DOCUMENTS

| | | | |
|---|---|---|---|
| 4,816,567 A | 3/1989 | Cabilly et al. | |
| 10,059,771 B2 * | 8/2018 | Mannent | A61K 39/395 |
| 2019/0177408 A1 | 6/2019 | Zheng et al. | |

FOREIGN PATENT DOCUMENTS

| | | |
|---|---|---|
| CN | 105377894 A | 6/2014 |
| CN | 106267190 A | 1/2017 |

(Continued)

OTHER PUBLICATIONS

McCarthy et al., J. Immunol. Methods, 251(1-2): 137-149 (Year: 2001).*

(Continued)

*Primary Examiner* — Adam Weidner
*Assistant Examiner* — Ashley H. Gao
(74) *Attorney, Agent, or Firm* — Cozen O'Connor

(57) ABSTRACT

Disclosed in the present application are an antibody or an antigen-binding portion thereof binding to human IL-4R, a polynucleotide encoding the antibody or antigen-binding portion thereof, a vector comprising the polynucleotide, a host cell comprising the polynucleotide or vector, a method for preparing and purifying the antibody, and the use of the antibody or antigen-binding portion thereof.

18 Claims, 5 Drawing Sheets

Specification includes a Sequence Listing.

(56) References Cited

FOREIGN PATENT DOCUMENTS

| CN | 107474134 A | 12/2017 |
|---|---|---|
| CN | 108373505 A | 8/2018 |
| RU | 2445318 C2 | 3/2012 |
| WO | WO 2008/054606 A2 | 5/2008 |

OTHER PUBLICATIONS

Lin et al. (African Journal of Biotechnology, 10(79):18294-18302) (Year: 2011).*
Autoimmune Disease, Cleveland Clinc, retrieved from: https://my.clevelandclinic.org/health/diseases/21624-autoimmune-diseases (Year: Last Updaed 2021) (Year: 2021).*
Highlights of Prescribing Information, DUPIXENT (Dupilumab), 13 pages.
Dupilumab Search Results Jun. 2, 2021, Clinicaltrials.gov, 11 pages.
Bourdin et al., Dupilumab is effective in type 2-high asthma patients receiving high-dose inhaled corticosteroids at baseline, *Allergy* 2021:76, European Journal of Allergy and Clinical Immunology and John Wiley & Sons Ltd, pp. 269-280.
Bawany et al., Dupilumab: One therapy to treat multiple atopic diseases, JAAD Case Reports, vol. 6, No. 11, Nov. 2020, pp. 1150-1152.
Ali et al., Dupilumab: a new contestant to corticosteroid in allergic bronchopulmonary aspergillosis, Oxford Medical Case Reports 2021;4, pp. 113-114.
Ferrucci et al., Clinical Response and Quality of Life in Patients with Severe Atopic Dermatitis Treated with Dupilumab: A Single-Center Real-Life Experience, Journal of Clinical Medicine 2020, 9, 791, Mar. 13, 2020, 10 pages.
Blum et al., Successful treatment of Brunsting-Perry pemphigoid with dupilumab, JAAD Case Reports, vol. 10, Apr. 2021, pp. 107-109.
Russian Patent Application No. 2020136302/10(066944), Office Action dated Apr. 23, 2021, 5 pages.
English translation of Russian Patent Application No. 2020136302/10(066944), Office Action dated Apr. 23, 2021, 4 pages.
Russian Patent Application No. 2020136302/10(066944), Patent Search Report dated Apr. 23, 2021, 2 pages.
English translation of Russian Patent Application No. 2020136302/10(066944), Patent Search Report dated Apr. 23, 2021, 2 pages.
International Patent Application No. PCT/CN2018/100263; International Search Report and Written Opinion dated Jan. 15, 2019; 21 pgs.
Howard, M., et al., *Identification of a T cell-derived b cell growth factor distinct from interleukin 2.* J Exp Med, 1982. 155(3): p. 914-23.
LaPorte, S.L., et al., *Molecular and structural basis of cytokine receptor pleiotropy in the interleukin-4/13 system.* Cell, 2008. 132(2): p. 259-72.
Nelms, K., et al., *The IL-4 receptor: signaling mechanisms and biologic functions.* Annu Rev Immunol, 1999. 17: p. 701-38.4.
Wynn, T.A., *IL-13 effector functions.* Annu Rev Immunol, 2003. 21: p. 425-56.
Punnonen, J., et al., *Interleukin 13 induces interleukin 4-independent IgG4 and IgE synthesis and CD23 expression by human B cells.* Proc Natl Acad Sci U S A, 1993. 90(8): p. 3730-4.
Zurawski, G. and J.E. de Vries, *Interleukin 13, an interleukin 4-like cytokine that acts on monocytes and B cells, but not on T cells.* Immunol Today, 1994. 15(1): p. 19-26.
Corren, J., *Role of interleukin-13 in asthma.* Curr Allergy Asthma Rep, 2013. 13(5): p. 415-20.
Obiri, N.I., et al., *Receptor for interleukin 13. Interaction with interleukin 4 by a mechanism that does not involve the common gamma chain shared by receptors for interleukins 2, 4, 7, 9, and 15.* J Biol Chem, 1995. 270(15): p. 8797-804.
Hilton, D.J., et al., *Cloning and characterization of a binding subunit of the interleukin 13 receptor that is also a component of the interleukin 4 receptor.* Proc Natl Acad Sci U S A, 1996. 93(1): p. 497-501.
Kraich, M., et al., *A modular interface of IL-4 allows for scalable affinity without affecting specificity for the IL-4 receptor.* BMC Biol, 2006. 4: p. 13.
Blakely, K., M. Gooderham, and K. Papp, *Dupilumab, A Monoclonal Antibody for Atopic Dermatitis: A Review of Current Literature.* Skin Therapy Lett, 2016. 21(2): p. 1-5.
Esnault, S., et al., *Differential spontaneous expression of mRNA for IL-4, IL-10, IL-13, IL-2 and interferon-gamma (IFN-gamma) in peripheral blood mononuclear cell(PBMC) from atopic patients.* Clin Exp Immunol, 1996. 103(1): p. 111-8.
Jujo, K., et al., *Decreased interferon gamma and increased interleukin-4 production in atopic dermatitis promotes IgE synthesis.* J Allergy Clin Immunol, 1992. 90(3 Pt 1): p. 323-31.
Chan, L.S., N. Robinson, and L. Xu, *Expression of interleukin-4 in the epidermis of transgenic mice results in a pruritic inflammatory skin disease: an experimental animal model to study atopic dermatitis.* J Invest Dermatol, 2001. 117(4): p. 977-83.
Zheng, T., et al., *Transgenic expression of interleukin-13 in the skin induces a pruritic dermatitis and skin remodeling.* J Invest Dermatol, 2009. 129(3): p. 742-51.
Howell, M.D., et al., *Cytokine modulation of atopic dermatitis filaggrin skin expression.* J Allergy Clin Immunol, 2007. 120(1): p. 150-5.
Sehra, S., et al., *IL-4 regulates skin homeostasis and the predisposition toward allergic skin inflammation.* J Immunol, 2010. 184(6): p. 3186-90.
Larche, M., D.S. Robinson, and A.B. Kay, *The role of T lymphocytes in the pathogenesis of asthma.* J Allergy Clin Immunol, 2003. 111(3): p. 450-63; quiz 464.
Kotsimbos, T.C., P. Ernst, and Q.A. Hamid, *Interleukin-13 and interleukin-4 are coexpressed in atopic asthma.* Proc Assoc Am Physicians, 1996. 108(5): p. 368-73.
Wills-Karp, M., Interleukin-13 in asthma pathogenesis. Curr Allergy Asthma Rep, 2004. 4(2): p. 123-31.
Grunig, G., et al., *Requirement for IL-13 independently of IL-4 in experimental asthma.* Science, 1998. 282(5397): p. 2261-3.
Wills-Karp, M., et al., *Interleukin-13: central mediator of allergic asthma.* Science, 1998. 282(5397): p. 2258-61.
Al-Lazikani et al., Standard Conformations for Canonical Structures of Immunoglobulins, J. Mol. Biol. 273:927-948 (1997).
Martin et al. "Modeling antibody hypervariable loops: A combined algorithm", Proc. Natl. Acad. Sci.USA86:9268-9272 (1989).
Morrison et al., "Chimeric human antibody molecules: Mouse antigen-binding domains with human constant region domains", Proc. Natl. Acad. Sci. USA 81:6851-6855 (1984).

* cited by examiner

ANTI-IL-4R ANTIBODY AND USE THEREOF

REFERENCE TO RELATED APPLICATION

This application is a 35 U.S.C. § 371 filing of International Application No. PCT/CN2018/100263 filed Aug. 13, 2018, which claims priority to Chinese Patent Application No. 201810360234.5 with the filing date being Apr. 20, 2018 and the title of invention being "ANTI-IL-4R ANTIBODY AND USE THEREOF", the entire contents of which are incorporated herein by reference.

TECHNICAL FIELD

The present application generally pertains to the field of genetic engineering and antibody drugs. In particular, the present application pertains to anti-human interleukin-4 receptor (IL-4R) antibodies and use thereof. The present application develops novel anti-human IL-4R antibodies and provides the use of the antibodies in the treatment of IL-4R-mediated diseases.

BACKGROUND

Interleukin-4 (IL-4) consists of 153 amino acids and has a molecular weight of about 17 kDa. Initially, IL-4 was found because its capability of stimulating the proliferation of B cells and was named B cell stimulating factor-1 (BSF-1)[1]. IL-4, like IL-13, belongs to type I cytokine family and has a quaternary structure consisting of a hydrophobic cluster core of 4α helices[2]. IL-4 is secreted by TH2 cells, participates in TH2-mediated immune responses, and has a wide range of biological activities including stimulating proliferation of T cells, mast cells, granulocytes, megakaryocytes, and erythrocytes[3]. In addition, IL-4 can stimulate B cells to express major histocompatibility complex class 2 molecules. IL-13 has approximately 30% amino acid sequence homology to IL-4 and multiple similar functions as IL-4. Both IL-4 and IL-13 promote B cell proliferation and work in combination with CD40/CD40L as co-stimulation to induce the conversion of IgM types to IgE[5]. IL-4 promotes mast cell aggregation, up-regulates expression of mast cell high affinity IgE receptor and IgE low affinity receptor CD23 (FcεRII) on B cells, up-regulates expression of vascular endothelial cell adhesion molecule (VCAM-1), and promotes migration of eosinophils, T lymphocytes, monocytes and basophils. Unlike IL-13, IL-4 can promote differentiation of naive T cells into TH2[6].

IL-4 requires binding to membrane receptors to biologically function. The human interleukin receptor (IL-4R) is a heterodimer formed from two polypeptide chains, one of which, a chain, has a high affinity for IL-4. Since the IL-4Rα chain plays a leading role in the binding of IL-4 to the IL-4R complex, IL-4Rα is commonly used as a substitution for IL-4R in many scientific studies and reports. IL-4R is expressed on a variety of cells such as human B cells, mast cells, eosinophils, basophils, macrophages/monocytes, DC cells, fibrocytes, airway epithelia, and smooth muscle. IL-4Rα can form two types of receptor complexes with other subunits. Type I receptors consisting of IL-4Rα and γc are mainly expressed in hematopoietic stem cells[3]. In non-hematopoietic stem cells, IL-4 functions primarily through type II receptors consisting of IL-4Ra and IL-13Ra1[8,9]. Type II receptors are co-receptors of IL-4 and IL-13. IL-13 binds to IL-13Rα1 to function. Both type I receptors and type II receptors signal through the Jak/STAT pathway. IL-4Rα, γc and IL-13Rα1 bind to Jak1, Jak3 and Tyk2, respectively, to activate downstream pathways. IL-4 and IL-13 can also signal through the insulin receptor substrate family (IRS), to ultimately activate PI3-K and NF-κB in the nucleus[10]. Blocking IL-4R can inhibit the biological function of both IL-4 and IL-13.

Several studies have shown that IL-4 and IL-13 are associated with diseases involving the TH2 immune response. Atopic dermatitis (AD), also known as genetically allergic dermatitis, is a common disease in dermatology and is prevalent in children and adolescents. AD is frequently companied with certain genetically allergic diseases such as allergic rhinitis, and asthma[11]. It was found that, in AD patients, the levels of TH2 factors, e.g. IL-4, IL-5, IL-10, and IL-13, increased[12], and the level of IgE increased[13]. It was also found that TH2 factors were associated with the progression of AD. Mice overexpressing TH2 factors, such as IL-4 and IL-13, showed skin protection deficiency and AD-like disorders[14][15]. Elevated levels of IL-4 and IL-13 in AD patients impeded epidermal differentiation and production of antimicrobial peptides. IL-4-deficient mice had reduced occurrence of skin allergic inflammation. These studies suggest that blocking IL-4R may be effective in the treatment of AD. Monoclonal antibodies against IL-4R have been marketed abroad, and shown good therapeutic effect on AD[11].

In addition, IL-13 and IL-4 play important roles in asthma. Asthma is a common pulmonary inflammatory disease characterized by airway hyperresponsiveness (AHR), mucus hypersecretion, fibrosis, and elevated IgE levels. Non-specific stimuli, such as cold air, often lead to increased airway hyperresponsiveness. AHR and excessive mucus secretion lead to airway obstruction, which is a major death cause in asthma. TH2 factors play important roles in the progression of asthma[18]. Bronchi and alveolar lavage fluids in asthma patients overexpress IL-4 and IL-13[19]. Although IL-13 and IL-4 have some functional similarity, some studies suggest that IL-13 plays a more important role in the progression of asthma than other Th2 cytokines[20]. IL-13 can promote differentiation and fibrosis of goblet cells. Injection of recombinant IL-13 into the airways of mice without allergen stimulation leads to airway inflammation, mucus hypersecretion and airway hyperresponsiveness[21, 22]. Injection of soluble IL13Rα2 can prevent the occurrence of AHR, mucus hypersecretion and lung inflammation in mice. Injection of an anti-IL-4Rα antibody in an asthma model reduces AHR and eosinophils in alveolar lavage fluids. Studies have shown that blocking IL-4Rα may be effective in the treatment of asthma.

The development and use of novel anti-IL-4R antibodies is desirable in the art.

SUMMARY OF THE INVENTION

In a first aspect, there is provided in the present application an antibody that binds to human IL-4R comprising a heavy chain variable region comprising HCDR1, HCDR2, and HCDR3 and a light chain variable region comprising LCDR1, LCDR2, and LCDR3, wherein the HCDR1 has the sequence of GFTFSSYAMS, the HCDR2 has the sequence of SITGGGGGIYYADSVKG, the HCDR3 has the sequence of DRISITIRPRYFGLDF, the LCDR1 has the sequence of RSSQSLLYSIGYNYLD, the LCDR2 has the sequence of LGSNRAS, and the LCDR3 has the sequence of MQSFKAPYT; or the HCDR1 has the sequence of GFTFSSYAMS, the HCDR2 has the sequence of SITGGGGGIYYADSVKG, the HCDR3 has the sequence of DRISITIRPRYFGLDF, the LCDR1 has the sequence of RSSRNVIYGNGYNYLD, the LCDR2 has the sequence of LGNNVAA, and the LCDR3 has the sequence of MQSLQAPYT; or the HCDR1 has the sequence of GFTFSSYAMS, the HCDR2 has the sequence of SITGGGGGIYYADSVKG, the HCDR3 has the sequence of DRISITIRPRYFGLDF, the LCDR1 has the sequence of RSSQNVYGNGYNYLD, the LCDR2 has the sequence of LGTNVAA, and the LCDR3 has the sequence of MQSLQAPYT; or the HCDR1 has the sequence of GFTFSSYAMS, the HCDR2 has the sequence of SITGGGGGIYYADSVKG, the HCDR3 has the sequence of DRISITIRPRYFGLDF, the LCDR1 has the sequence of RSSQNVYGNGYNYLD, the LCDR2 has the sequence of LGNNVAA, and the LCDR3 has the sequence of MQSLKAPYT; or the HCDR1 has the sequence of GFTFSSYAMS, the HCDR2 has the sequence of SITGGGGGIYYADSVKG, the HCDR3 has the sequence of DRISITIRPRYFGLDF, the LCDR1 has the sequence of RSSHNLLYSNGYNYLD, the LCDR2 has the sequence of LGSNRAY, and the LCDR3 has the sequence of MQALQSPYT;

the HCDR1 has the sequence of GFTFSSYAMS, the HCDR2 has the sequence of SITGGGGGIYYADSVKG, the HCDR3 has the sequence of DRISITIRPRYFGLDF, the LCDR1 has the sequence of RSSQSLLYSNGYNYLD, the LCDR2 has the sequence of LGSNRAS, and the LCDR3 has the sequence of MQALETPYA;

wherein the HCDR and LCDR are defined according to Kabat.

In some embodiments, the heavy chain variable region of the antibody has the amino acid sequence of SEQ ID NO: 18.

In some embodiments, the light chain variable region of the antibody has the amino acid sequence of SEQ ID NO: 26, 27, 28, 29, 30, or 31.

In some embodiments, the heavy chain variable region of the antibody has the amino acid sequence of SEQ ID NO: 18 and the light chain variable region of the antibody has the amino acid sequence of SEQ ID NO: 26.

In some embodiments, the heavy chain variable region of the antibody has the amino acid sequence of SEQ ID NO: 18 and the light chain variable region of the antibody has the amino acid sequence of SEQ ID NO: 27.

In some embodiments, the heavy chain variable region of the antibody has the amino acid sequence of SEQ ID NO: 18 and the light chain variable region of the antibody has the amino acid sequence of SEQ ID NO: 28.

In some embodiments, the heavy chain variable region of the antibody has the amino acid sequence of SEQ ID NO: 18 and the light chain variable region of the antibody has the amino acid sequence of SEQ ID NO: 29.

In some embodiments, the heavy chain variable region of the antibody has the amino acid sequence of SEQ ID NO: 18 and the light chain variable region of the antibody has the amino acid sequence of SEQ ID NO: 30.

In some embodiments, the heavy chain variable region of the antibody has the amino acid sequence of SEQ ID NO: 18 and the light chain variable region of the antibody has the amino acid sequence of SEQ ID NO: 31.

In a second aspect, there is provided in the present application an antibody that binds to human IL-4R, wherein the amino acid sequence of the heavy chain variable region of the antibody is at least 90% identical to SEQ ID NO: 18 and the amino acid sequence of the light chain variable region of the antibody is at least 90% identical to any one of SEQ ID NO: 26, 27, 28, 29, 30, or 31.

In some embodiments of the first aspect and the second aspect, the antibody is directed against IL4Rα.

In some embodiments of the first aspect and the second aspect, the antibody is capable of binding to recombinant human IL4R (SEQ ID NO: 1) and recombinant monkey IL4R (SEQ ID NO: 3), and has a KD of less than 1 nM when binding to recombinant human IL4R.

In some embodiments of the first aspect and the second aspect, the antibody is capable of inhibiting the activation of HEK-Blue IL-4/IL-13 cells by recombinant IL4 (SEQ ID NO: 4) with an $IC_{50}$ value of less than 100 pM.

In some embodiments of the first aspect and the second aspect, the antibody is capable of inhibiting the activation of HEK-Blue IL-4/IL-13 cells by recombinant IL13 (SEQ ID NO: 32) with an $IC_{50}$ value of less than 50 pM.

In some embodiments of the first aspect and the second aspect, the antibody is capable of inhibiting the proliferation of TF-1 cells induced by recombinant IL4 (SEQ ID NO: 4) with an $IC_{50}$ value of less than 200 pM.

In some embodiments of the first aspect and the second aspect, the antibody is an intact antibody, a Fab fragment, a $F(ab')_2$ fragment, or a single chain Fv fragment (scFv).

In some embodiments of the first aspect and the second aspect, the antibody is a fully human antibody.

In some embodiments of the first aspect and the second aspect, the antibody further comprises a heavy chain constant region of an IgG1 subtype, an IgG2 subtype, or an IgG4 subtype and/or a light chain constant region of a κ subtype or a λ subtype.

In some embodiments of the first aspect and the second aspect, the antibody is a monoclonal antibody.

In some embodiments of the first aspect and the second aspect, the antibody is a neutralizing antibody.

In some embodiments of the first to second aspects, the antibody is capable of binding to and neutralizing human IL4R, thereby blocking IL4-IL4R and IL13-IL4R signaling pathways.

In a third aspect, there is provided in the present application a nucleic acid molecule encoding an antibody in the first aspect and the second aspect or an antigen-binding portion thereof.

In a fourth aspect, there is provided in the present application a pharmaceutical composition comprising an antibody in the first aspect and the second aspect and a pharmaceutically acceptable excipient, diluent or carrier.

In some embodiments, the pharmaceutical composition is for use in the treatment of an IL-4R-mediated disease.

In a fifth aspect, there is provided in the present application the use of an antibody in the first and second aspects in the manufacture of a medicament for the prevention or treatment of an IL-4R-mediated disease.

In a sixth aspect, there is provided in the present application a method of preventing or treating an IL-4R-mediated disease, comprising administering to a subject in need thereof an antibody in the first aspect and the second aspect or a pharmaceutical composition in the fourth aspect.

In some embodiments of the fourth aspect, the fifth aspect, and the sixth aspect, the IL-4R-mediated disease is an autoimmune disease. In some embodiments, the autoimmune disease is asthma or allergic dermatitis.

SEQUENCE DESCRIPTION

Figure 1:
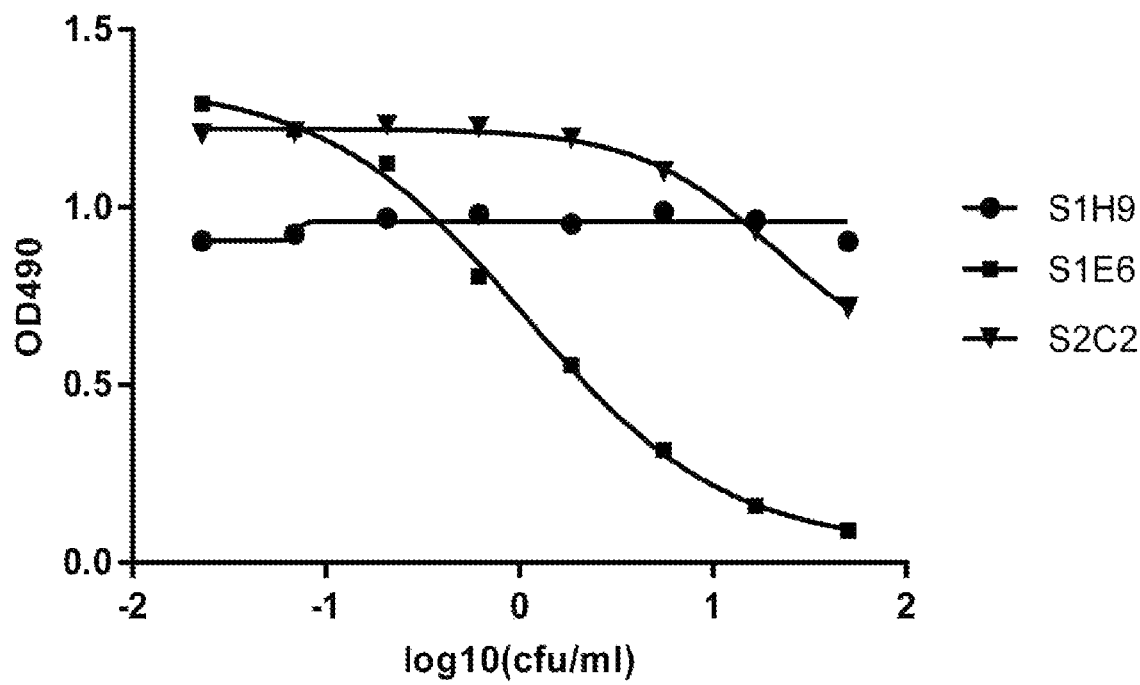
FIG. 1 shows an IL4R-binding epitope assay of exemplary anti-IL4R phage-scFvs of the present application.

SEQ ID NO: 1 shows the amino acid sequence of human (*Homo sapiens*) IL-4R extracellular domain (hIL-4R).

SEQ ID NO: 2 shows the amino acid sequence of murine (*Mus musculus*) IL-4R extracellular domain (mIL-4R).

SEQ ID NO: 3 shows the amino acid sequence of *Macaca mulatta* IL-4R extracellular domain (mmIL-4R).

SEQ ID NO: 4 shows the amino acid sequence of human IL-4 extracellular domain (hIL-4).

SEQ ID NO: 5 shows the amino acid sequence of His tag (His).

SEQ ID NO: 6 shows the amino acid sequence of the Fc region (Fc) of a human IgG1 antibody.

SEQ ID NO: 7 shows the amino acid sequence of the Fc region (mFc) of a murine IgG2a antibody.

SEQ ID NO: 8 shows the amino acid sequence of the heavy chain constant region of human IgG1 subtype.

SEQ ID NO: 9 shows the amino acid sequence of the heavy chain constant region of human IgG2 subtype.

SEQ ID NO: 10 shows the amino acid sequence of the heavy chain constant region of human IgG4 subtype.

SEQ ID NO: 11 shows the amino acid sequence of the heavy chain constant region of murine IgG1 subtype.

SEQ ID NO: 12 shows the amino acid sequence of the heavy chain constant region of murine IgG2a subtype.

SEQ ID NO: 13 shows the amino acid sequence of the light chain constant region of human kappa (κ) subtype.

SEQ ID NO: 14 shows the amino acid sequence of the light chain constant region of human lambda (λ) subtype.

SEQ ID NO: 15 shows the amino acid sequence of the light chain constant region of murine kappa (κ) subtype.

SEQ ID NO: 16 shows the amino acid sequence of the light chain constant region of murine lambda (λ) subtype.

SEQ ID NO: 17, SEQ ID NO: 18 and SEQ ID NO: 19 show the full-length amino acid sequence, VH amino acid sequence, and VL amino acid sequence of clone S1E6, respectively.

SEQ ID NO: 20, SEQ ID NO: 21, SEQ ID NO: 22 show the full-length amino acid sequence, VH amino acid sequence, and VL amino acid sequence of clone S1H9, respectively.

SEQ ID NO: 23, SEQ ID NO: 24, SEQ ID NO: 25 show the full-length amino acid sequence, VH amino acid sequence, and VL amino acid sequence of clone S2C2, respectively.

SEQ ID NO: 26 shows the amino acid sequence of light chain mutant L18D7.

SEQ ID NO: 27 shows the amino acid sequence of light chain mutant L28G5.

SEQ ID NO: 28 shows the amino acid sequence of light chain mutant L28F8.

SEQ ID NO: 29 shows the amino acid sequence of light chain mutant L28C9.

SEQ ID NO: 30 shows the amino acid sequence of the light chain mutant L10B2.

SEQ ID NO: 31 shows the amino acid sequence of light chain mutant L10C2.

SEQ ID NO: 32 shows the amino acid sequence of human recombinant IL-13.

DETAILED DESCRIPTION OF THE INVENTION

The inventors of the present application have developed novel anti-human IL-4R antibodies by antibody engineering techniques. In various aspects of the present application, novel anti-human IL-4R antibodies or antigen-binding fragments thereof, polynucleotides encoding the antibodies or antigen-binding fragments, vectors comprising the polynucleotides, host cells comprising the polynucleotides or vectors, methods of preparing and purifying the antibodies, and medical and biological use of the antibodies or antigen-binding fragments are provided. Based on the sequences of the variable regions of the antibodies provided herein, full-length antibody molecules can be constructed and used as medicaments for the treatment of clinical diseases mediated by IL-4R.

Unless otherwise indicated, the inventions can be practiced using conventional molecular biology, microbiology, cell biology, biochemistry, and immunological techniques in the art.

Unless otherwise indicated, the terms used in the present application have the meanings commonly understood by those skilled in the art.

DEFINITIONS

As used herein, the term "antibody" refers to an immunoglobulin molecule that is capable of specifically binding to a target via at least one antigen recognition site located in a variable region of the immunoglobulin molecule. Targets include, but are not limited to, carbohydrates, polynucleotides, lipids, and polypeptides. As used herein, an "antibody" includes not only an intact (i.e., full-length) antibody, but also an antigen-binding fragment thereof (e.g., Fab, Fab', F(ab')$_2$, Fv), a variant thereof, a fusion protein comprising portions of an antibody, a humanized antibody, a chimeric antibody, a diabody, a linear antibody, a single-chain antibody, a multi-specific antibody (e.g., a bi-specific antibody), and any other modified formats of an immunoglobulin molecule comprising a desired specific antigen recognition site, including a glycosylated variant of an antibody, an amino acid sequence variant of an antibody, and a covalently modified antibody.

Typically, an intact or full-length antibody comprises two heavy chains and two light chains. Each heavy chain contains a heavy chain variable region (VH) and first, second and third constant regions (CH1, CH2 and CH3). Each light chain contains a light chain variable region (VL) and a constant region (CL). A full-length antibody may be of any type, such as an IgD, IgE, IgQ IgA, or IgM (or their subtypes) antibody, but not necessarily belong to any particular type. Immunoglobulins can be assigned to different types depending on their amino acid sequences of the heavy chain constant domains. Generally, immunoglobulins have five main types, i.e., IgA, IgD, IgE, IgQ and IgM, and some of these types can be further classified into subtypes (isotypes), such as IgG1, IgG2, IgG3, IgG4, IgA1, and IgA2. Heavy chain constant domains corresponding to individual immunoglobulin types are referred to as α, δ, ε, γ, and μ, respectively. Subunit structures and three-dimensional structures of different types of immunoglobulins are well known.

As used herein, the term "antigen-binding fragment" or "antigen-binding portion" refers to a portion or region of an intact antibody molecule responsible for binding to an antigen. An antigen binding domain can comprise a heavy chain variable region (VH), a light chain variable region (VL), or both. Each of VH and VL typically contains three complementarity determining regions, i.e., CDR1, CDR2, and CDR3.

It is well known to those skilled in the art that complementarity determining regions (CDRs, usually including CDR1, CDR2 and CDR3) are the regions of a variable region that have mostly impact on the affinity and specificity of an antibody. The CDR sequences of VH or VL have two common definitions, i.e., the Kabat definition and the Chothia definition (see, e.g., Kabat, "Sequences of Proteins of Immunological Interest", National Institutes of Health, Bethesda, Md. (1991); Al-Lazikani et al., J. Mol. Biol. 273: 927-948 (1997); and Martin et al., Proc. Nal. Acad. Sci. USA 86: 9268-9272 (1989)). For the variable region sequences of a given antibody, the sequences of CDR regions in the VH and VL can be determined according to the Kabat definition or the Chothia definition. In some embodiments of the present application, CDR sequences are defined according toKabat.

For the variable region sequences of a given antibody, the sequences of CDR regions in the variable region sequences can be analyzed in a variety of ways, for example, using online software Abysis.

Examples of an antigen-binding fragment include, but are not limited to, (1) an Fab fragment, which can be a monovalent fragment having a VL-CL chain and a VH-CH1 chain; (2) an F(ab')₂ fragment, which can be a divalent fragment having two Fab' fragments linked by a disulfide bridge of the hinge region (i.e., a dimer of Fab'); (3) an Fv fragment having VL and VH domains in a single arm of an antibody; (4) a single chain Fv (scFv), which can be a single polypeptide chain consisting of a VH domain and a VL domain via a polypeptide linker; and (5) (scFv)₂, which can comprise two VH domains linked by a peptide linker and two VL domains that are combined with the two VH domains via a disulfide bridge.

As used herein, the term "specific binding" refers to a non-random binding reaction between two molecules, e.g., binding of an antibody to an antigen epitope.

As used herein, the term "monoclonal antibody" refers to an antibody from a substantially homogeneous antibody population, i.e., antibodies constituting the population are the same except for naturally occurring mutations which may be present in a small number of individual antibodies. Monoclonal antibodies described herein particularly include "chimeric" antibodies in which a portion of the heavy and/or light chain is identical or homologous to a corresponding sequence in an antibody derived from a particular species or belonging to a particular antibody type or subtype, while the remainder of the heavy and/or light chain is identical or homologous to a corresponding sequence in an antibody derived from another species or belonging to another antibody type or subtype, and also include fragments of such antibodies as long as they exhibit desired biological activity (U.S. Pat. No. 4,816,567; and Morrison et al., Proc. Nal. Acad. Sci. USA 81: 6851-6855 (1984)).

Degenerate bases (besides conventional bases A, T, C, and G) are used in the nucleic acid sequences described herein and have the same meanings as commonly understood by those skilled in the art. For example, R represents A or G; Y represents C or T, M represents A or C; K represents G or T; S represents C or G; W represents A or T; H represents A or C or T; B represents C or G or T; V represents A or C or G; D represents A or G or T; N represents A or C or G or T.

In a first aspect, there is provided in the present application an antibody that binds to human IL-4R comprising a heavy chain variable region comprising HCDR1, HCDR2, and HCDR3 sequences and a light chain variable region comprising LCDR1, LCDR2, and LCDR3 sequences, wherein the HCDR1 has the sequence of GFTFSSYAMS, the HCDR2 has the sequence of SITGGGGGIYYADSVKG, the HCDR3 has the sequence of DRISMRPRYFGLDF, the LCDR1 has the sequence of RSSQSLLYSIGYNYLD, the LCDR2 has the sequence of LGSNRAS, and the LCDR3 has the sequence of MQSFKAPYT; or the HCDR1 has the sequence of GFTFSSYAMS, the HCDR2 has the sequence of SITGGGGGIYYADSVKG, the HCDR3 has the sequence of DRISMRPRYFGLDF, the LCDR1 has the sequence of RSSRNVIYGNGYNYLD, the LCDR2 has the sequence of LGNNVAA, and the LCDR3 has the sequence of MQSLQAPYT; or the HCDR1 has the sequence of GFTFSSYAMS, the HCDR2 has the sequence of SITGGGGGIYYADSVKG, the HCDR3 has the sequence of DRISMRPRYFGLDF, the LCDR1 has the sequence of RSSQNVYGNGYNYLD, the LCDR2 has the sequence of LGTNVAA, and the LCDR3 has the sequence of MQSLQAPYT; or the HCDR1 has the sequence of GFTFSSYAMS, the HCDR2 has the sequence of SITGGGGGIYYADSVKG, the HCDR3 has the sequence of DRISMRPRYFGLDF, the LCDR1 has the sequence of RSSQNVYGNGYNYLD, the LCDR2 has the sequence of LGNNVAA, and the LCDR3 has the sequence of MQSLKAPYT; or the HCDR1 has the sequence of GFTFSSYAMS, the HCDR2 has the sequence of SITGGGGGIYYADSVKG, the HCDR3 has the sequence of DRISMRPRYFGLDF, the LCDR1 has the sequence of RSSHNLLYSNGYNYLD, the LCDR2 has the sequence of LGSNRAY, and the LCDR3 has the sequence of MQALQSPYT;

the HCDR1 has the sequence of GFTFSSYAMS, the HCDR2 has the sequence of SITGGGGGIYYADSVKG, the HCDR3 has the sequence of DRISMRPRYFGLDF, the LCDR1 has the sequence of RSSQSLLYSNGYNYLD, the LCDR2 has the sequence of LGSNRAS, and the LCDR3 has the sequence of MQALETPYA;

wherein the HCDR and LCDR are defined according to Kabat.

In some embodiments, the heavy chain variable region of the antibody has the amino acid sequence of SEQ ID NO: 18.

In some embodiments, the light chain variable region of the antibody has the amino acid sequence of SEQ ID NO: 26, 27, 28, 29, 30, or 31.

In some embodiments, the heavy chain variable region of the antibody has the amino acid sequence of SEQ ID NO: 18 and the light chain variable region of the antibody has the amino acid sequence of SEQ ID NO: 26.

In some embodiments, the heavy chain variable region of the antibody has the amino acid sequence of SEQ ID NO: 18 and the light chain variable region of the antibody has the amino acid sequence of SEQ ID NO: 27.

In some embodiments, the heavy chain variable region of the antibody has the amino acid sequence of SEQ ID NO: 18 and the light chain variable region of the antibody has the amino acid sequence of SEQ ID NO: 28.

In some embodiments, the heavy chain variable region of the antibody has the amino acid sequence of SEQ ID NO: 18 and the light chain variable region of the antibody has the amino acid sequence of SEQ ID NO: 29.

In some embodiments, the heavy chain variable region of the antibody has the amino acid sequence of SEQ ID NO: 18 and the light chain variable region of the antibody has the amino acid sequence of SEQ ID NO: 30.

In some embodiments, the heavy chain variable region of the antibody has the amino acid sequence of SEQ ID NO: 18 and the light chain variable region of the antibody has the amino acid sequence of SEQ ID NO: 31.

In a second aspect, there is provided in the present application an antibody that binds to human IL-4R, wherein the amino acid sequence of the heavy chain variable region of the antibody is at least 90% identical to SEQ ID NO: 18 and the amino acid sequence of the light chain variable region of the antibody is at least 90% identical to any one of SEQ ID NO: 26, 27, 28, 29, 30, or 31.

In some embodiments of the first aspect and the second aspect, the antibody is directed against IL-4Rα.

In some embodiments of the first aspect and the second aspect, the antibody is capable of binding to recombinant human IL4R (SEQ ID NO: 1) and recombinant monkey IL4R (SEQ ID NO: 3), and has a KD of less than 1 nM when binding to recombinant human IL4R.

In some embodiments of the first aspect and the second aspect, the antibody is capable of inhibiting the activation of HEK-Blue IL-4/IL-13 cells by recombinant IL4 (SEQ ID NO: 4) with an $IC_{50}$ value of less than 100 pM.

In some embodiments of the first aspect and the second aspect, the antibody is capable of inhibiting the activation of HEK-Blue IL-4/IL-13 cells by recombinant IL13 (SEQ ID NO: 32) with an $IC_{50}$ value of less than 50 pM.

In some embodiments of the first aspect and the second aspect, the antibody is capable of inhibiting the proliferation of TF-1 cells induced by recombinant IL4 (SEQ ID NO: 4) with an $IC_{50}$ value of less than 200 pM.

In some embodiments of the first aspect and the second aspect, the antibody is an intact antibody, a Fab fragment, a F(ab')$_2$ fragment, or a single chain Fv fragment (scFv).

In some embodiments of the first aspect and the second aspect, the antibody is a fully human antibody.

In some embodiments of the first aspect and the second aspect, the antibody further comprises a heavy chain constant region of an IgG1 subtype, an IgG2 subtype, or an IgG4 subtype and/or a light chain constant region of a κ subtype or a λ subtype.

In some embodiments of the first aspect and the second aspect, the antibody is a monoclonal antibody.

In some embodiments of the first aspect and the second aspect, the antibody is a neutralizing antibody.

In some embodiments of the first to second aspects, the antibody is capable of binding to and neutralizing human IL4R, thereby blocking IL4-IL4R and IL13-IL4R signaling pathways.

In a third aspect, there is provided in the present application a nucleic acid molecule encoding an antibody of the first aspect and the second aspect or an antigen-binding portion thereof.

In some embodiments, the nucleic acid molecule is operably linked to a regulation sequence that can be recognized by a host cell transformed with a vector.

In a fourth aspect, there is provided in the present application a pharmaceutical composition comprising an antibody of the first aspect and the second aspect and a pharmaceutically acceptable excipient, diluent or carrier.

In some embodiments, the pharmaceutical composition may further comprise one or more of a lubricant, such as talc, magnesium stearate, and mineral oil; a wetting agent; an emulsifier; a suspending agent; a preservative such as benzoic acid, sorbic acid and calcium propionate; a sweetening agent and/or a flavoring agent.

In some embodiments, the pharmaceutical composition herein may be formulated as a tablet, a pill, a powder, a lozenge, an elixir, a suspension, an emulsion, a solution, a syrup, a suppository, or a capsule.

In some embodiments, the pharmaceutical composition of the present application may be delivered using any physiologically acceptable administration route including, but not limited to, oral administration, parenteral administration, nasal administration, rectal administration, intraperitoneal administration, intravascular injection, subcutaneous administration, transdermal administration, or inhalation administration.

In some embodiments, a pharmaceutical composition for therapeutic use may be formulated for storage in a lyophilized formulation or in the form of an aqueous solution by mixing an agent with desired purity with a pharmaceutically acceptable carrier or excipient where appropriate.

In some embodiments, the pharmaceutical composition is used to treat an IL-4R mediated disease.

In a fifth aspect, there is provided in the present application the use of an antibody of the first to second aspects in the manufacture of a medicament for the prevention or treatment of an IL-4R mediated disease.

In a sixth aspect, there is provided in the present application a method of preventing or treating an IL-4R mediated disease, comprising administering to a subject in need thereof an antibody of the first aspect and the second aspect or a pharmaceutical composition of the fourth aspect.

In some embodiments of the fourth aspect, the fifth aspect, and the sixth aspect, the IL-4R mediated disease is an autoimmune disease. In some embodiments, the autoimmune disease is asthma or allergic dermatitis.

In other aspects, there is provided in the present application a vector comprising an isolated nucleic acid molecule encoding an antibody or an antigen-binding portion thereof of the present application, and a host cell comprising the nucleic acid molecule or vector.

In other aspects, there is provided in the present application a method of producing an antibody of the present application. In some embodiments, a method of producing an antibody comprises culturing a host cell to facilitate expression of a nucleic acid. In some embodiments, a method of producing an antibody further comprises recovering the antibody from a culture medium of host cell.

It is to be understood that the foregoing detailed description is intended only to enable those skilled in the art to have better understanding of the present application and is not intended to cause limitations in any way. Various modifications and variations can be made to the described embodiments by those skilled in the art.

The following Examples are for purposes of illustration only and are not intended to limit the scope of the present application.

EXAMPLES

Example 1. Construction of Phage Display Antibody Library

This Examples was carried out according to Chinese patent applications 201610609651.X (title of invention "Anti-human PDL1 antibody and use thereof") and 201510097117.0 (title of invention "Anti-human IL-17 monoclonal antibody") previously filed by the inventors. The contents of the above two patent applications are incorporated herein by reference.

Example 2: Preparation of Recombinant Proteins

A number of recombinant proteins were used in the preparation and tests of anti-IL-4R monoclonal antibodies, including human IL-4R extracellular domain (hIL-4R, SEQ ID NO: 1), murine IL-4R extracellular domain (mIL-4R, SEQ ID NO: 2), *Macaca mulatta* IL-4R extracellular domain (mmIL-4R, SEQ ID NO: 3), human IL-4 extracellular domain (hIL-4, SEQ ID NO: 4) and human recombinant IL-13 (SEQ ID NO: 32). These proteins all have post-translational modifications (e.g., glycosylation or disulfide bonds), and thus use of mammalian cell expression systems would be more advantageous in maintaining the structure and function of the recombinant proteins. In addition, a His tag (His, SEQ ID NO: 5), a Fc region of a human IgG1 antibody (Fc, SEQ ID NO: 6) or a Fc region of a murine IgG2a antibody (mFc, SEQ ID NO: 7) was added at the C-terminuses of these recombinant proteins, which facilitated purification of the recombinant proteins and functional identification of monoclonal antibodies. An antibody heavy chain constant region may be of human IgG1 subtype (SEQ ID NO: 8), human IgG2 subtype (SEQ ID NO: 9), human IgG4 subtype (SEQ ID NO: 10) or murine IgG1 subtype (SEQ ID NO: 11), or murine IgG2a subtype (SEQ ID NO: 12), and a light chain constant region may be of human κ subtype (SEQ ID NO: 13), human λ subtype (SEQ ID NO: 14), murine κ subtype (SEQ ID NO: 15), or murine λ subtype (SEQ ID NO: 16).

According to the amino acid sequences of individual recombinant proteins of interest in the Uniprot database, genes (including a His tag or a Fc or mFc encoding gene) of the recombinant proteins described above were designed and synthesized. The synthesized genes of individual recombinant proteins were cloned into suitable eukaryotic expression vectors (such as pcDNA3.1, Invitrogen, Inc.) using conventional molecular biology techniques. The prepared recombinant protein expression plasmids were then transfected into HEK293 cells (such as HEK293F, Invitrogen, Inc.) using liposomes (such as 293 fectin, Invitrogen, Inc.) or other cationic transfection reagents (such as PEI). The cells were cultured in suspension in serum-free mediums for 3-4 days. The culture supernatants were then harvested by centrifugation.

The expressed fusion recombinant proteins with His-tags were subjected to a metal chelate affinity chromatography column (e.g., HisTrap FF, GE, Inc.) for one-step purification of the recombinant proteins in the culture supernatant. The expressed fusion recombinant proteins with FC and mFc were subjected to one-step purification using Protein A/G affinity chromatography columns (e.g., Mabselect SURE, GE, Inc.). The preservation buffers of recombinant proteins were then replaced with PBS (pH 7.0) or other suitable buffers using a desalting column (such as Hitrap desaulting, GE, Inc.). If necessary, the antibody samples may be sterilized by filtration and then stored in aliquots at −20° C.

Example 3: Screening of Anti-Human IAR Monoclonal Antibodies Using Phage Display Antibody Library Technology 3.1 Screening of Anti-Human IL4R Monoclonal Antibodies The recombinant hIL4R-his prepared in Example 2 was used as the antigen. By using a solid phase screening strategy (experimental protocol described in phage display: General experimental guidelines/(US) Clackson, T., (US) Lowman, H. B.) Editing; Ma Lan et al. Chemical Industry Press, 2005.) to screen the phage display library of human single chain antibody library prepared in Example 1, three human antibodies having different sequences but capable of specifically binding to human IL4R were obtained, including clone S1E6 (the amino acid sequence is shown in SEQ ID NO: 17, the VH sequence is shown in SEQ ID NO: 18, and the VL sequence is shown in SEQ ID NO: 19), S1H9 (the amino acid sequence is shown in SEQ ID NO: 20, the VH sequence is shown in SEQ ID NO: 21, the VL sequence is shown in SEQ ID NO: 22), S2C2 (the amino acid sequence is shown in SEQ ID NO: 23, the VH sequence SEQ ID NO: is shown in 24, and the VL sequence is shown in SEQ ID NO: 25).

3.2 Primary Functional Analysis of Anti-Human IL4R Monoclonal Antibodies (Protein Level)

The three monoclonal antibodies S1E6, S1H9 and S2C2 were prepared into purified phage (phage-scFv) and contacted with coated recombinant IL4R antigen. Different monoclonal antibody phage-scFvs at a fixed titer were subjected to the recombinant IL4 at a series of concentration gradients, respectively. The HRP-anti-M13 secondary antibody was used to detect the ability of the recombinant IL4 to block the binding of the three monoclonal antibody phage-scFvs to IL4R. The results (FIG. 1) show that, the recombinant IL4 competes with the S1E6 phage-scFv for binding to IL4R, indicating that the S1E6 single chain antibody and IL4 have similar IL4R binding sites.

3.3 Primary Functional Assay of Recombinant Anti-Human IL4R Monoclonal Antibodies (Cellular Level)

The HEK-Blue™ IL-4/IL-13 cell (InvivoGen, hkb-il 413) is a reporter cell strain developed by InvivoGen based on HEK293 cells. The cell strain is stably transduced with human STAT6 gene and SEAP (base phosphatase) reporter. When interleukin-4 (IL-4) or interleukin-13 (IL-13) stimulates the cells, the STAT6 signal pathway in the cells is activated, the SEAP reporter is induced to express, and SEAP is synthesized and secreted into the cell supernatant.

The SEAP concentration can be quantitatively analyzed by a microplate reader at 630 nm.

Figure 2:
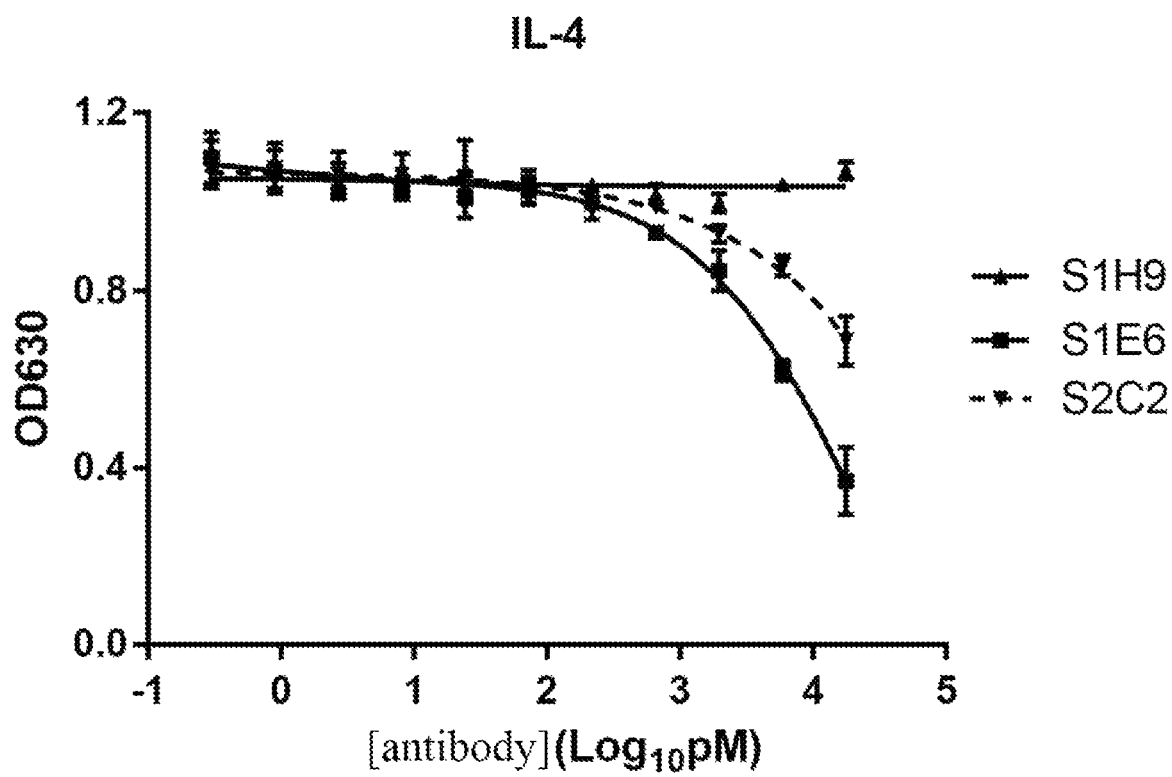
FIG. 2 shows the graph of inhibition of IL-4-induced SEAP expression in HEK-Blue IL-4/IL-13 cells by exemplary anti-IL4R monoclonal antibodies of the present application.
Figure 3:
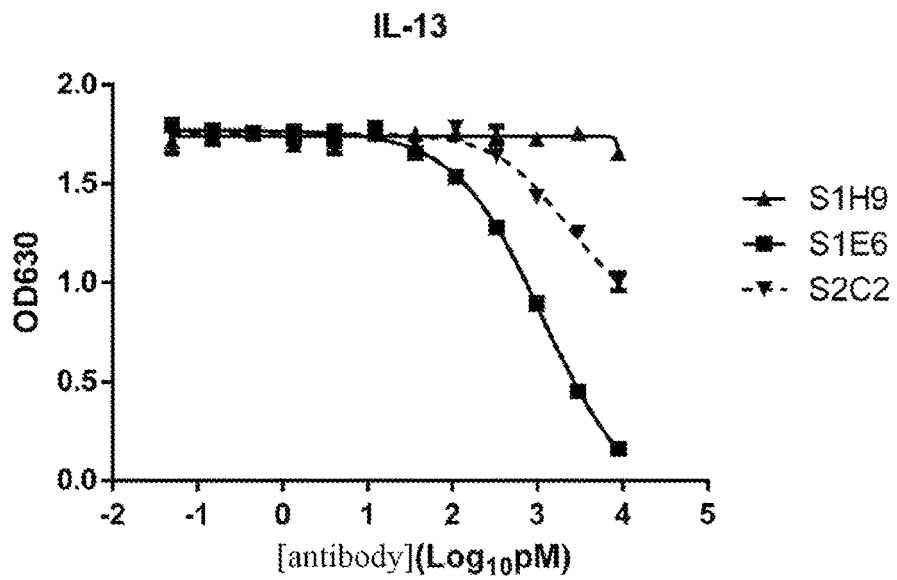
FIG. 3 shows the graph of inhibition of IL-13 induced SEAP expression in HEK-Blue IL-4/IL-13 cells by exemplary anti-IL4R monoclonal antibodies of the present application.

This Example evaluated the ability of different recombinant anti-IL4R monoclonal antibodies (heavy chain constant region of human IgG4 subtype) to inhibit IL-4 and IL-13 using HEK-Blue™ IL-4/IL-13 cells. Each well of a 96-well plate was seeded with $5 \times 10^4$ HEK-Blue™ IL-4/IL-13 cells, and the cells were stimulated with IL-4 (40 pM) or IL-13 (80 pM). Anti-IL4R monoclonal antibodies at a series of concentration gradients were added to block IL-4 or IL-13. The results of FIG. 2 and FIG. 3 show that monoclonal antibody S1E6 has the strongest ability to block IL-4 and IL-13, S2C2 is weaker than S1E6, and S1H9 is unable to block stimulation of HEK-Blue™ IL-4/IL-13 cells by IL-4 and IL-13.

Example 4: Affinity Maturation of Anti-Human IL4R Monoclonal Antibodies 4.1 In Vitro Affinity Maturation of Antibody S1E6 Based on Light Chain CDR Mutation and Light Chain Substitution Strategy The S1E6 monoclonal antibody was subjected to in vitro affinity maturation using a two-vector phage display system based on light chain CDR (LCDR) mutation strategy (see, Example 5 in Chinese Patent Application No. 201510097117.0 filed earlier by the applicant for details). A S1E6VK-CDR123 mutant library with a library capacity of over 1.4×10E8 was constructed by classical overlap extension PCR. The primers for introducing mutations in the three CDRs of the light chain of SE6 (SE6VK) are shown in Table 5. This light chain mutation library was then subjected to three rounds of screening using recombinant hIL4R-His as antigen. Finally, four high-affinity light chain mutants L18D7 (amino acid sequence shown in SEQ ID NO: 26), L28G5 (amino acid sequence shown in SEQ ID NO: 27), L28F8 (amino acid sequence shown in SEQ ID NO: 28) and L28C9 (amino acid sequence shown in SEQ ID NO: 29) were identified.

TABLE 5

Primers for constructing the SLE6 light chain LCDR mutation library

| PRIMER NAME | PRIMER SEQUENCE |
| --- | --- |
| PWM04-S1E6VK-CDR 123F1 | ATGCCATGGCGGACATCGTGATG ACACAGAGC (SEQ ID NO: 50) |
| PWM04-S1E6VK-CDR 123R1 | TACCAGTCCAGGTAGTTGTAGCC AWTASYGKWGABGABANTKYGGC TGCTTCTACAGCTGATGCT (SEQ ID NO: 51) |
| PWM04-S1E6VK-CDR 123F2 | GGCTACAACTACCTGGACTGGTA (SEQ ID NO: 52) |
| PWM04-S1E6VK-CDR 123R2 | ATCTATCGGGCACGCCGKMGNCA MCABTGKWAVCCAGGTAGATCAG CAGCTGAGG (SEQ ID NO: 53) |
| PWM04-S1E6VK-CDR 123F3 | GGCGTGCCCGATAGAT (SEQ ID NO: 54) |
| PWM04-S1E6VK-CDR 123R3 | CCTGGCCAAAGGTGTAAGGAGHT YKKAAGGMCTGCATACAGTAGTA GAAGCCCA (SEQ ID NO: 55) |
| PWM04-S1E6VK-CDR 123R4 | CGTACGCTTGATTTCCAGCTTGG TGCCCTGGCCAAAGGTGTAAGG (SEQ ID NO: 56) |

Meanwhile, with the heave chain of the antibody S1E6, in vitro affinity maturation studies were done using a two-vector phage display system based on a light chain substitution strategy (see Example 4.3 in Chinese Patent Application No. 201510097117.0 filed earlier by the applicant for details). Two high-affinity light chain mutants L10B2 (amino acid sequence shown in SEQ ID NO: 30) and L10C2 (amino acid sequence shown in SEQ ID NO: 31) were obtained.

4.2 Functional Analysis of Anti-IL4R Monoclonal Antibody Recombinant Proteins

Recombinant whole human antibodies in human IgG4-kappa form were prepared by conventional molecular biological methods from the light chain mutants which bind to IL4R with high affinity obtained from 4.1.

Figure 4:
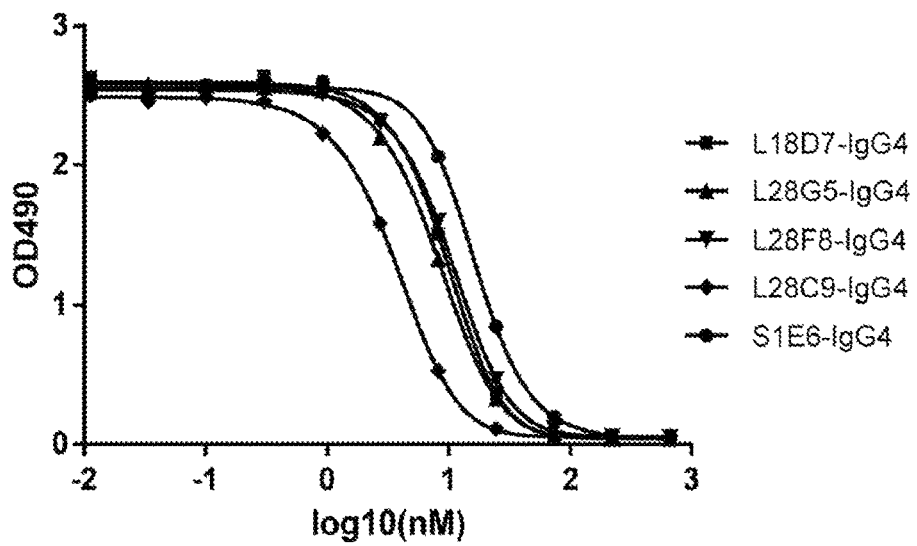
FIG. 4 shows that an exemplary light chain mutant S1E6 of the present application inhibits the binding between IL4 and IL4R.
Figure 5:
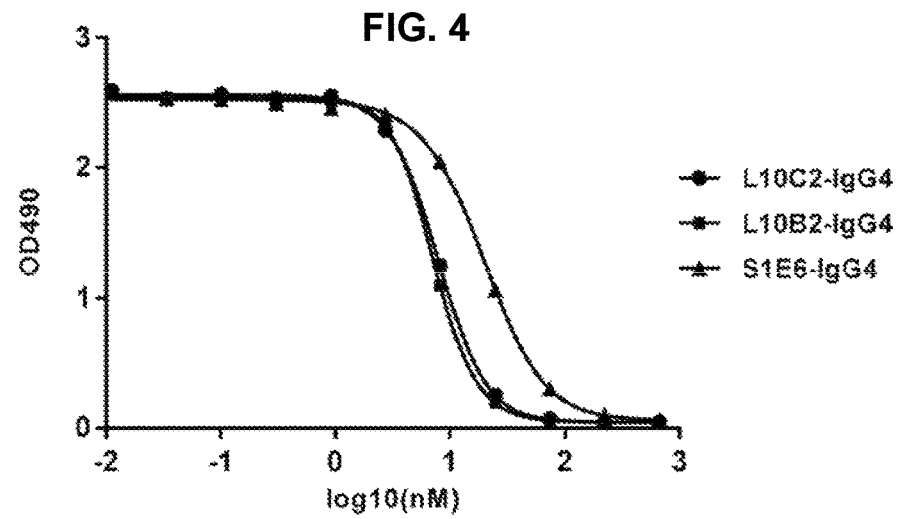
FIG. 5 shows that an exemplary light chain mutant S1E6 of the present application inhibits the binding between IL4 and IL4R.

96 well plates were coated with antigen IL4R-mFc (3 μg/ml, 100 μl/well) overnight at 4° C. Each anti-IL4R recombinant antibody was diluted at a gradient with IL4-his at a fixed concentration, and added to a 96-well plate at 100 μl/well and incubated at 37° C. for 1 h. HRP-mouse-anti-his IgG (Kangweishiji, CW0285M) was used to detect binding of IL4-his to IL4R-mFc. ELISA analysis results (FIG. 4 and FIG. 5) show that the six light chain mutants of S1E6 were able to effectively block the binding of IL4R to IL4, and were superior to S1E6. $IC_{50}$ is shown in Table 6 and Table 7.

TABLE 6

$IC_{50}$ in inhibition of IL4 binding to IL4R by S1E6 light chain mutants

|  | L18D7 | L28G5 | L28F8 | L28C9 | S1E6 |
| --- | --- | --- | --- | --- | --- |
| $IC_{50}$ | 9.682 | 8.304 | 10.78 | 3.755 | 16.6 |

TABLE 7

$IC_{50}$ in inhibition of IL4 binding to IL4R by S1E6 light chain mutants

|  | L10C2 | L10B2 | S1E6 |
| --- | --- | --- | --- |
| $IC_{50}$ | 7.879 | 7.166 | 19.77 |

4.3 Affinity Analysis of Anti-IL4R Monoclonal Antibodies

The affinity of each anti-IL4R IgG4 chimeric antibody was determined using Biacore X100. Amino coupling kits, human antibody capture kits, CM5 chips, 10× HBS-EP (pH 7.4) and all reagents used in this assay were purchased from GE Healthcare. According to the instructions in the kits, an antibody against the human Fc region was coupled to the surface of the CM5 chip using an amino coupling method, and antibody proteins were diluted to appropriate concentrations to ensure that about 100 RU of the antibodies was captured by the antibody against the human Fc. IL4R-his was set to a series of concentration gradients (100 nm, 33.3 nm, 11.1 nm, 3.7 nm, 1.23 nm) and flew through the surface of the stationary phase. The chip surface was regenerated with 3M $MgCl_2$, and the affinity of each monoclonal antibody was measured at 25° C. The biacore data were analyzed using Biacore X100 Evaluation software (version 2.0.1) and the fitting results are shown in Table 8 and Table 9.

TABLE 8

Affinity constants of huIL4R binding of anti-IL4R monoclonal antibodies (light chain substitution mutants)

| | $K_{on}$ (1/MS) | $K_{off}$ (1/s) | KD (M) |
|---|---|---|---|
| L10B2-IgG4 | 3.432E+5 | 1.520E−4 | 4.429E−10 |
| L10C2-IgG4 | 3.531E+5 | 3.085E−4 | 8.736E−10 |
| S1E6-IgG4 | 3.125E+5 | 9.227E−4 | 2.953E−9 |

TABLE 9

Affinity constants of huIL4R binding of anti-IL4R monoclonal antibodies (LCDR mutants)

| | $K_{on}$ (1/Ms) | $K_{off}$ (1/s) | KD (M) |
|---|---|---|---|
| L18D7-IgG4 | 2.97E5 | 1.426E−4 | 4.8E−10 |
| L28F8-IgG4 | 3.422E5 | 1.436E−4 | 4.196E−10 |
| L28G5-IgG4 | 2.891E5 | 1.343E−4 | 4.645E−10 |
| L28C9-IgG4 | 3.307E5 | 1.937E−4 | 5.857E−10 |
| S1E6-IgG4 | 2.494E5 | 7.086E−4 | 2.841E−9 |

Similarly, anti-IL4R monoclonal antibodies were captured and mmIL4R-mFc was set to a series of concentration gradient (50 nm, 16.7 nm, 5.56 nm, 31.85 nm, 0.62 nm). The affinity data for each anti-IL4R monoclonal antibody in binding to mmIL4R were as shown in Table 10.

| | $K_{on}$ (1/Ms) | $K_{off}$ (1/s) | KD (M) |
|---|---|---|---|
| L18D7-IgG4 | 5.904E5 | 9.839E−4 | 1.667E−9 |
| L28C9-IgG4 | 7.065E5 | 5.935E−3 | 8.401E−9 |
| L28F8-IgG4 | 7.485E5 | 5.189E−3 | 6.932E−9 |
| L28G5-IgG4 | 6.842E5 | 7.086E−3 | 1.036E−8 |
| S1E6-IgG4 | 5.271E5 | 4.904E−3 | 9.305E−9 |

4.4 Cytological Function Analysis of anti-IL4R Monoclonal Antibodies

Figure 6:
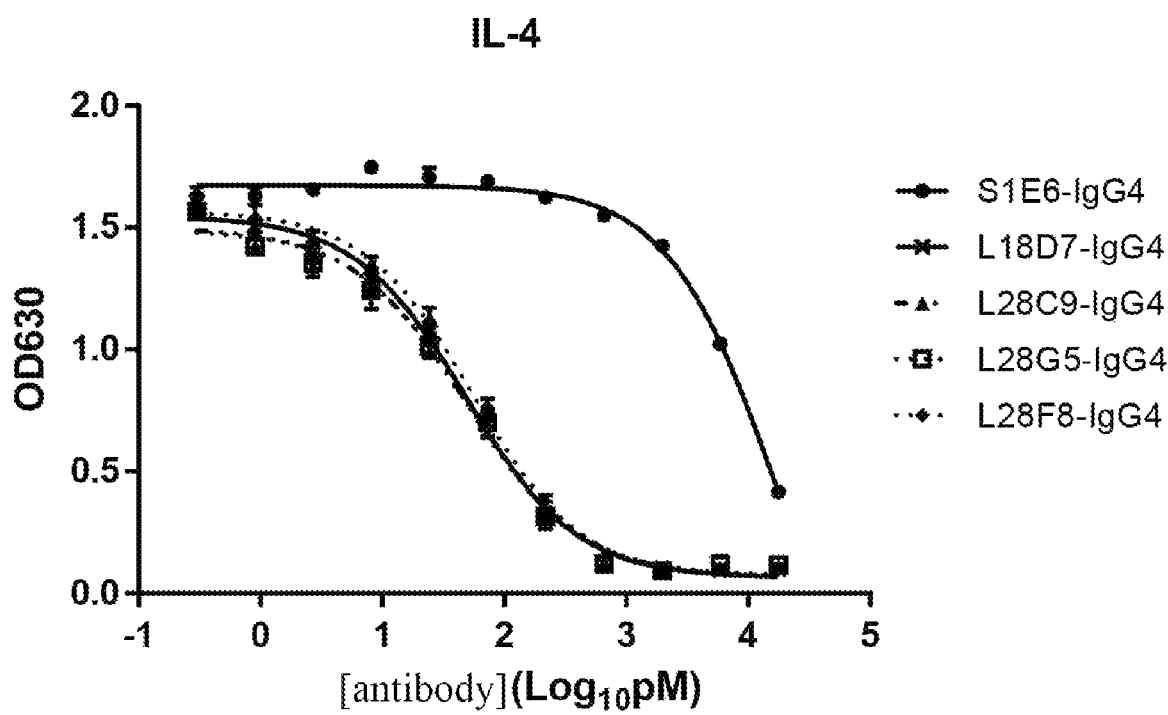
FIG. 6 shows the graph of inhibition of IL-4-induced SEAP expression in HEK-Blue IL-4/IL-13 cells by an exemplary light chain mutant S1E6 of the present application.
Figure 7:
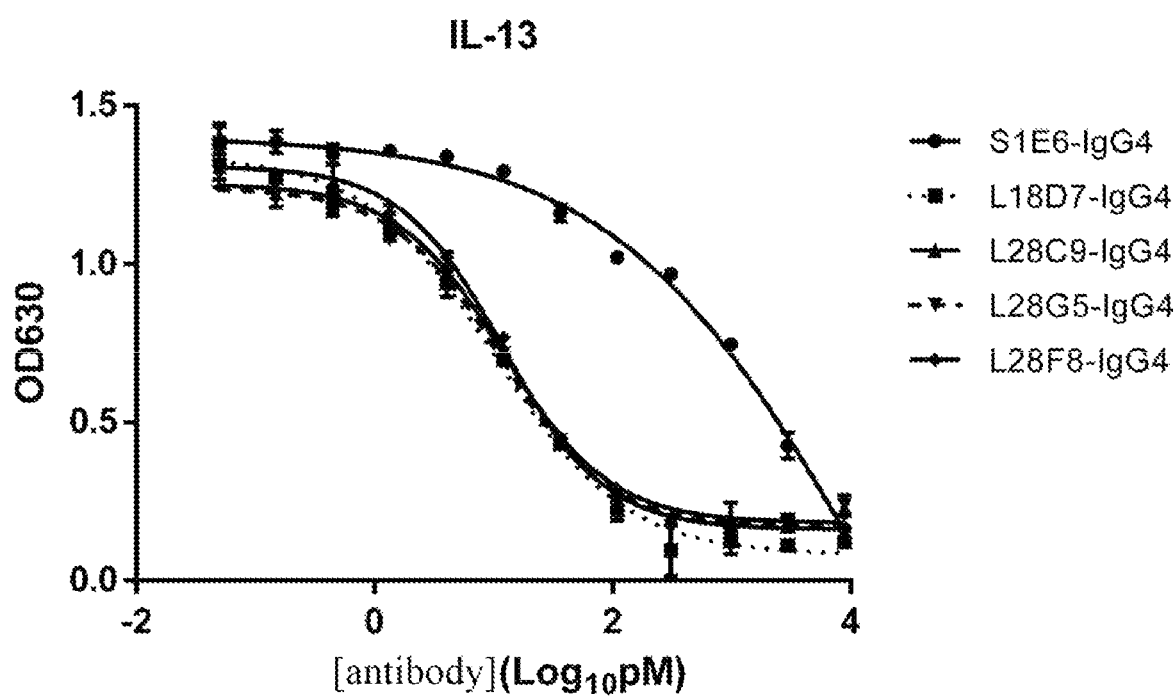
FIG. 7 shows the graph of inhibition of IL-13 induced SEAP expression in HEK-Blue IL-4/IL-13 cells by an exemplary light chain mutant S1E6 of the present application.
Figure 8:
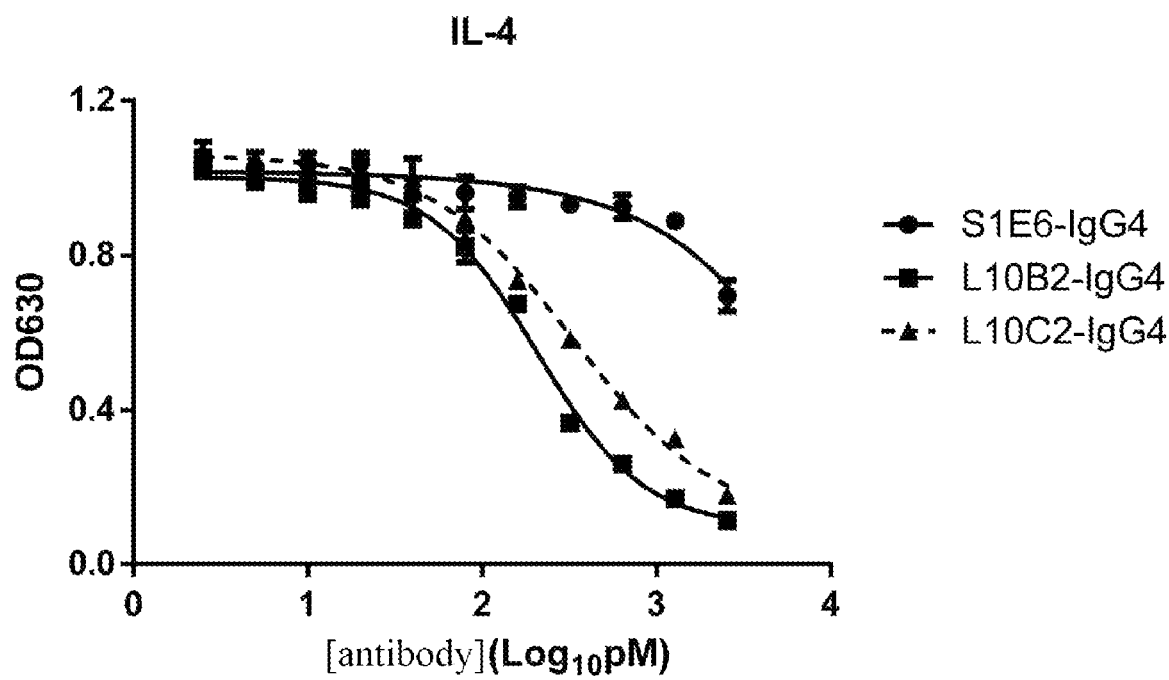
FIG. 8 shows the graph of inhibition of IL-4-induced SEAP expression in HEK-Blue IL-4/IL-13 cells by an exemplary light chain mutant S1E6 of the present application.
Figure 9:
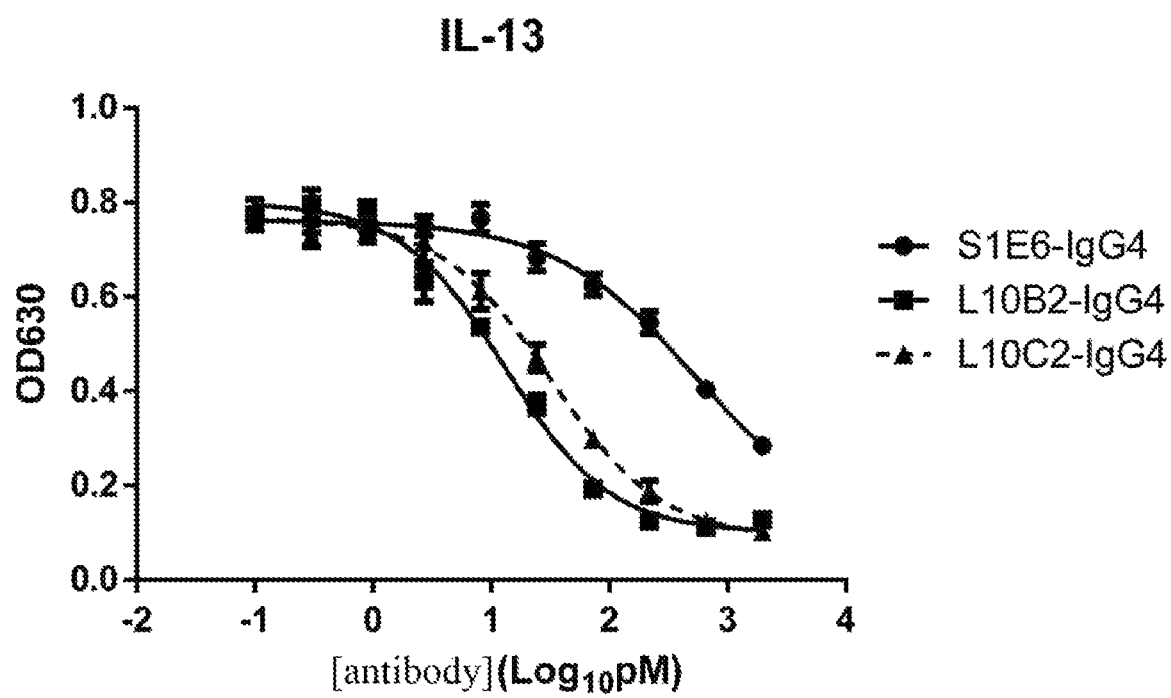
FIG. 9 shows the graph of inhibition of IL-13 induced SEAP expression in HEK-Blue IL-4/IL-13 cells by an exemplary light chain mutant S1E6 of the present application.

4.4.1 Analysis of Biological Activity of anti-IL4R Monoclonal Antibodies Based on HEK-Blue IL-4/IL-13 Cells Detailed experimental protocols are described in Example 3.3. The results (FIG. 6 and FIG. 7) show that four SE6 light chain mutants have significantly increased biological activity as compared with S1E6, and that the $IC_{50}$ values of the four S1E6 light chain mutants in inhibition of IL-4 or IL-13 are similar (Table 11 and Table 12). The results of FIGS. 8 and 9 show that the activity of IL-4 and IL-13 is enhanced by the other two SLE6 light chain mutants, L10B2 is superior to L10C2, the $IC_{50}$ values of Table 13 show that L10C2 inhibits IL-4 by 1.6-fold compared to L10B2, and the $IC_{50}$ values of Table 14 show that L10C2 inhibits IL-13 by 2.4-fold compared to L10B2.

TABLE 11

$IC_{50}$ values in inhibition of IL-4 by S1E6 light chain mutants

| IL-4 | S1E6-IgG4 | L18D7-IgG4 | L28C9-IgG4 | L28G5-IgG4 | L28F8-IgG4 |
|---|---|---|---|---|---|
| $IC_{50}$ (pM) | ~ | 48.39 | 49.40 | 48.41 | 55.02 |

TABLE 12

$IC_{50}$ values in inhibition of IL-13 by S1E6 light chain mutants

| IL-13 | S1E6-IgG4 | L18D7-IgG4 | L28C9-IgG4 | L28G5-IgG4 | L28F8-IgG4 |
|---|---|---|---|---|---|
| $IC_{50}$ (pM) | ~ | 10.20 | 12.12 | 11.51 | 12.07 |

TABLE 13

$IC_{50}$ values in inhibition of IL-4 by S1E6 light chain mutants

| IL-4 | S1E6-IgG4 | L10B2-IgG4 | L10C2-IgG4 |
|---|---|---|---|
| $IC_{50}$ (pM) | ~ | 206.7 | 332.8 |

TABLE 14

$IC_{50}$ values in inhibition of IL-13 by S1E6 light chain mutants

| IL-13 | S1E6-IgG4 | L10B2-IgG4 | L10C2-IgG4 |
|---|---|---|---|
| $IC_{50}$ (pM) | ~ | 13.05 | 31.42 |

Figure 10:
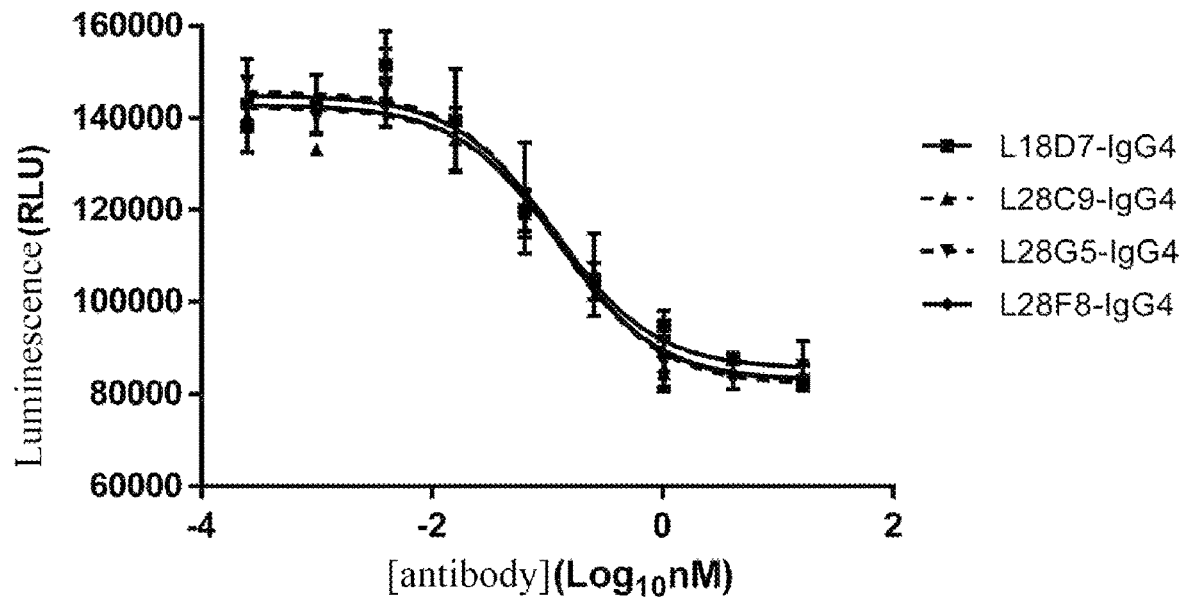
FIG. 10 shows that an exemplary light chain mutant S1E6 of the present application inhibits IL-4 induced proliferation of TF-1 cells.

4.4.2 Biological Activity of Anti-IL4R Monoclonal Antibodies Based on TF-1 Cell Proliferation Assay Human erythroleukemia cell line (TF-1) was established by Kitamura et al. in 1989. TF-1 cells used in the experiment were from the ATCC cell bank (CRL-2003). The growth of TF-1 cells is entirely dependent on GM-CSF or IL-3. Erythropoietin (EPO) can also maintain short-term growth of TF-1 cells, but does not induce differentiation of TF-1 cells. In addition, a variety of cytokines have effects on TF-1 cells, and cytokines such as IL-4 and IL-13 can stimulate proliferation of TF-1 cells. Each well of a 96-well plate was seeded with $2 \times 10^4$ cells. TF-1 cells were stimulated with IL-4 (80 pM), and anti-IL-4R monoclonal antibodies at a series of gradients (concentration range of 65.536 nM to 0.25 pM, four-fold dilution) were added. The number of viable cells was determined using the CellTiter-Glo™ cell viability assay kit (Promega, G7571). The results of FIG. 10 show that the graph of inhibition of TF-1 proliferation by four S1E6 light chain mutants are almost identical, with no significant difference in $IC_{50}$ values as shown in Table 15.

TABLE 15

$IC_{50}$ values in inhibition of IL-4 by S1E6 light chain mutants

| | L18D7-IgG4 | L28C9-IgG4 | L28G5-IgG4 | L28F8-IgG4 |
|---|---|---|---|---|
| $IC_{50}$ (nM) | 0.1159 | 0.1289 | 0.1181 | 0.1236 |

4.4.3 Analysis of Biological Activity of Anti-IL4R Monoclonal Antibodies Based on PBMC CD23 (FcεRII) is a cell surface receptor with low affinity for IgE and is expressed on the surfaces of a variety of inflammatory cells. Upregulation of CD23 expression increases the uptake and presentation of antigens in bronchial mucosa, leading to allergic reactions. IL-4 can stimulate up-regulation of CD23 expression on the surfaces of monocytes, macrophages and B lymphocytes.

Figure 11:
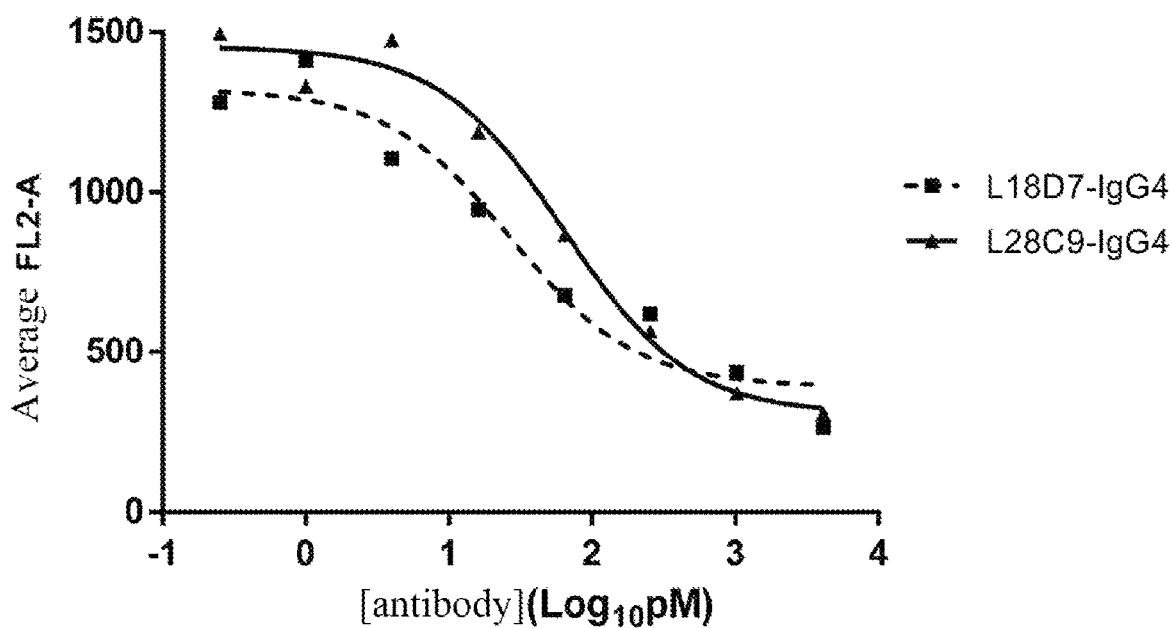
FIG. 11 shows that an exemplary light chain mutant S1E6 of the present application inhibit IL-4 induced CD23 expression in human PBMCs.

PBMCs were isolated from whole blood samples from healthy human subjects by Ficoll density gradient centrifugation. PBMC cells were stimulated with IL-4 (100 pM). Anti-IL-4R monoclonal antibodies at a series of gradient (maximum concentration of 16384 pM, and four-fold dilutions to 0.25 pM) were added. Cells were incubated for 48 h at 37° C. in 5% $CO_2$ environment, then harvested, and stained with anti-CD23-PE (BD Pharmingen, 555711). Expression of CD23 on PBMC was determined by flow cytometry (BD Accuri™ C6). The results of FIG. 11 show that L18D7 has a stronger ability to inhibit CD23 expression on PBMCs than L28C9, which inhibits IL-4 with an $IC_{50}$ value of 2.3-fold higher than L18D7.

TABLE 16

$IC_{50}$ values in inhibition of CD23 expression on human PBMCs by S1E6 light chain mutants

|  | L18D7-IgG4 | L28C9-IgG4 |
| --- | --- | --- |
| $IC_{50}$ (pM) | 26.82 | 63.48 |

REFERENCES

1. Howard, M., et al., Identification of a T cell-derived b cell growth factor distinct from interleukin 2. J Exp Med, 1982. 155 (3): P. 914-23.
2. LaPorte, S. L., et al., Molecular and structural basis of cytokine receptor pleiotropy in the interleukin-4/13 system. Cell, 2008. 132 (2): P. 259-72.
3. Nelms, K., et al., The IL-4 receptor: Signaling mechanisms and biologic functions. Annu Rev Immunol, 1999. 17: P. 701-38.4. Wynn, T. A., IL-13 effector functions. Annu Rev Immunol, 2003. 21: P. 425-56.
5. Punnonen, J., et al., Interleukin 13 induces interleukin 4—independent IgG4 and IgE synthesis and CD23 expression by human B cells. Proc Nal Acad Sci USA, 1993. 90 (8): P. 3730-4.
6. Zurawski, G and J. E. de Vries, Interleukin 13, an interleukin 4-like cytokine that acts on monocytes and B cells, but not on T cells. Immunol Today, 1994. 15 (1): P. 19-26.
7. Corren, J., Role of interleukin-13 in asthma. Curr Allergy Asthma Rep, 2013. 13 (5): P. 415-20.
8. Obiri, N. I., et al., Receptor for interleukin 13. Interaction with interleukin 4 by a mechanism that does not involve the common gamma chain shared by receptors for interleukins 2, 4, 7, 9, and 15. J Biol Chem, 1995. 270 (15): P. 8797-804.
9. Hilton, D. J., et al., Cloning and characterization of a binding subunit of the interleukin 13 receptor that is also a component of the interleukin 4 receptor. Proc Nal Acad Sci USA, 1996. 93 (1): P. 497-501.
10. Kraich, M., et al., A modular interface of IL-4 allows for scalable affinity without affecting specificity for the IL-4 receptor. BMC Biol, 2006. 4: P. 13.
11. Blakely, K., M. Gooderham, and K. Papp, Dupilumab, A Monoclonal Antibody for Atopic Dermatitis: A Review of Current Literature. Skin Therapy Lett, 2016. 21 (2): P. 1-5.
12. Esnault, S., et al., Differential spontaneous expression of mRNA for IL-4, IL-10, IL-13, IL-2 and interferon-gamma (IFN-gamma) in peripheral blood mononuclear cell (PBMC) from atopic patients. Clin Exp Immunol, 1996. 103 (1): P. 111-8.
13. Jujo, K., et al., Decreased interferon gamma and increased interleukin-4 production in atopic dermatitis promotes IgE synthesis. J Allergy Clin Immunol, 1992. 90 (3 Pt 1): P. 323-31.
14. Chan, L. S., N. Robinson, and L. Xu, Expression of interleukin-4 in the epidermis of transgenic mice results in a pruritic inflammatory skin disease: An experimental animal model to study atopic dermatitis. J Invest Dermatol, 2001. 117 (4): P. 977-83.
15. Zheng, T., et al., Transgenic expression of interleukin-13 in the skin induces a pruritic dermatitis and skin remodeling. J Invest Dermatol, 2009. 129 (3): P. 742-51.
16. Howell, M. D., et al., Cytokine modulation of atopic dermatitis filaggrin skin expression. J Allergy Clin Immunol, 2007. 120 (1): P. 150-5.
17. Sehra, S., et al., IL-4 regulates skin homeostasis and the predisposition toward allergic skin inflammation. J Immunol, 2010. 184 (6): P. 3186-90.
18. Larche, M., D. S. Robinson, and A. B. Kay, The role of T lymphocytes in the pathogenesis of asthma. J Allergy Clin Immunol, 2003. 111 (3): P. 450-63; quiz 464.
19. Kotsimbos, T. C., P. Emst, and Q. A. Hamid, Interleukin-13 and interleukin-4 are coexpressed in atopic asthma. Proc Assoc Am Physicians, 1996. 108 (5): P. 368-73.
20. Wills-Karp, M., Interleukin-13 in asthma pathogenesis. Curr Allergy Asthma Rep, 2004. 4 (2): P. 123-31.
21. Grunig, G, et al., Requirement for IL-13 independently of IL-4 in experimental asthma. Science, 1998. 282 (5397): P. 2261-3.
22. Wills-Karp, M., et al., Interleukin-13: Central mediator of allergic asthma. Science, 1998. 282 (5397): P. 2258-61.

What is claimed is:

1. An antibody that binds to human IL-4R comprising a heavy chain variable region comprising HCDR1, HCDR2 and HCDR3 and a light chain variable region comprising LCDR1, LCDR2 and LCDR, wherein
   the HCDR1 has the sequence of GFTFSSYAMS (SEQ ID NO: 33), the HCDR2 has the sequence of SITGGGG-GIYYADSVKG (SEQ ID NO: 34), the HCDR3 has the sequence of DRISITIRPRYFGLDF (SEQ ID NO: 35), the LCDR1 has the sequence of RSSQSLLYSIGY-NYLD (SEQ ID NO: 36), the LCDR2 has the sequence of LGSNRAS (SEQ ID NO: 37), and the LCDR3 has the sequence of MQSFKAPYT (SEQ ID NO: 38); or
   the HCDR1 has the sequence of GFTFSSYAMS (SEQ ID NO: 33), the HCDR2 has the sequence of SITGGGG-GIYYADSVKG (SEQ ID NO: 34), the HCDR3 has the sequence of DRISITIRPRYFGLDF (SEQ ID NO: 35), the LCDR1 has the sequence of RSSRNVIYGNGY-NYLD (SEQ ID NO: 39), the LCDR2 has the sequence of LGNNVAA (SEQ ID NO: 40), and the LCDR3 has the sequence of MQSLQAPYT (SEQ ID NO: 41); or
   the HCDR1 has the sequence of GFTFSSYAMS (SEQ ID NO: 33), the HCDR2 has the sequence of SITGGGG-GIYYADSVKG (SEQ ID NO: 34), the HCDR3 has the sequence of DRISITIRPRYFGLDF (SEQ ID NO: 35), the LCDR1 has the sequence of RSSQNVYGNGY-NYLD (SEQ ID NO: 42), the LCDR2 has the sequence of LGTNVAA (SEQ ID NO: 43), and the LCDR3 has the sequence of MQSLQAPYT (SEQ ID NO: 41); or
   the HCDR1 has the sequence of GFTFSSYAMS (SEQ ID NO: 33), the HCDR2 has the sequence of SITGGGG-GIYYADSVKG (SEQ ID NO: 34), the HCDR3 has the sequence of DRISITIRPRYFGLDF (SEQ ID NO: 35), the LCDR1 has the sequence of RSSQNVYGNGY-NYLD (SEQ ID NO: 42), the LCDR2 has the sequence of LGNNVAA (SEQ ID NO: 40), and the LCDR3 has the sequence of MQSLKAPYT (SEQ ID NO: 44); or
   the HCDR1 has the sequence of GFTFSSYAMS (SEQ ID NO: 33), the HCDR2 has the sequence of SITGGGG-GIYYADSVKG (SEQ ID NO: 34), the HCDR3 has the sequence of DRISITIRPRYFGLDF (SEQ ID NO: 35), the LCDR1 has the sequence of RSSHNLLYSNGY-NYLD (SEQ ID NO: 45), the LCDR2 has the sequence of LGSNRAY (SEQ ID NO: 46), and the LCDR3 has the sequence of MQALQSPYT (SEQ ID NO: 47);
   the HCDR1 has the sequence of GFTFSSYAMS (SEQ ID NO: 33), the HCDR2 has the sequence of SITGGGG-GIYYADSVKG (SEQ ID NO: 34), the HCDR3 has the sequence of DRISITIRPRYFGLDF (SEQ ID NO: 35), the LCDR1 has the sequence of RSSQSLLYSNGY-NYLD (SEQ ID NO: 48), the LCDR2 has the sequence of LGSNRAS (SEQ ID NO: 37), and the LCDR3 has the sequence of MQALETPYA (SEQ ID NO: 49);
   wherein the HCDR and LCDR are defined according to Kabat.

2. The antibody of claim 1, wherein the heavy chain variable region of the antibody has the amino acid sequence of SEQ ID NO: 18.

3. The antibody of claim 1, wherein the light chain variable region of the antibody has the amino acid sequence of SEQ ID NO: 26, 27, 28, 29, 30, or 31.

4. The antibody of claim 1, wherein
   the heavy chain variable region of the antibody has the amino acid sequence of SEQ ID NO: 18, and the light chain variable region of the antibody has the amino acid sequence of SEQ ID NO: 26; or
   the heavy chain variable region of the antibody has the amino acid sequence of SEQ ID NO: 18, and the light chain variable region of the antibody has the amino acid sequence of SEQ ID NO: 27; or
   the heavy chain variable region of the antibody has the amino acid sequence of SEQ ID NO: 18, and the light chain variable region of the antibody has the amino acid sequence of SEQ ID NO: 28; or
   the heavy chain variable region of the antibody has the amino acid sequence of SEQ ID NO: 18, and the light chain variable region of the antibody has the amino acid sequence of SEQ ID NO: 29; or
   the heavy chain variable region of the antibody has the amino acid sequence of SEQ ID NO: 18, and the light chain variable region of the antibody has the amino acid sequence of SEQ ID NO: 30; or
   the heavy chain variable region of the antibody has the amino acid sequence of SEQ ID NO: 18, and the light chain variable region of the antibody has the amino acid sequence of SEQ ID NO: 31.

5. The antibody of claim 1, wherein
   the antibody is capable of binding to recombinant human IL4R (SEQ ID NO: 1) and recombinant monkey IL4R (SEQ ID NO: 3) and has a KD of less than 1 nM when binding to recombinant human IL4R.

6. The antibody of claim 1, wherein the antibody is capable of inhibiting the activation of HEK-Blue IL-4/IL-13 cells by recombinant IL4 (SEQ ID NO: 4) with an $IC_{50}$ value below 100 pM.

7. The antibody of claim 1, wherein the antibody is capable of inhibiting the activation of HEK-Blue IL-4/IL-13 cells by recombinant IL13 (SEQ ID NO: 32) with an $IC_{50}$ value below 50 pM.

8. The antibody of claim 1, wherein the antibody is capable of inhibiting the proliferation of TF-1 cells induced by recombinant IL4 (SEQ ID NO: 4) with an $IC_{50}$ value below 200 pM.

9. The antibody of claim 1, wherein the antibody is an intact antibody, a Fab fragment, a F(ab')$_2$ fragment or a single chain Fv fragment (scFv).

10. The antibody of claim 1, wherein the antibody further comprises a heavy chain constant region of an IgG1 subtype, an IgG2 subtype or an IgG4 subtype and/or a light chain constant region of a κ subtype or a λ subtype.

11. The antibody of claim 1, wherein the antibody is a monoclonal antibody.

12. The antibody of claim 1, wherein the antibody binds to and neutralizes human IL4R, thereby blocking IL4-IL4R and IL13-IL4R signaling pathways.

13. A nucleic acid molecule encoding the antibody of claim 1.

14. A pharmaceutical composition comprising the antibody of claim 1 and a pharmaceutically acceptable excipient, diluent or carrier.

15. A method of treating an IL-4R-mediated disease comprising administering to a subject in need thereof the antibody of claim 1.

16. The method of claim 15, wherein the IL-4R-mediated disease is an autoimmune disease.

17. The method of claim 15, wherein the IL-4R-mediated disease is asthma or allergic dermatitis.

18. The antibody of claim 1, wherein the antibody is a fully human antibody.

* * * * *

SEQUENCE LISTING

```
<160> NUMBER OF SEQ ID NOS: 56

<210> SEQ ID NO 1
<211> LENGTH: 207
<212> TYPE: PRT
<213> ORGANISM: Homo sapiens

<400> SEQUENCE: 1

Met Lys Val Leu Gln Glu Pro Thr Cys Val Ser Asp Tyr Met Ser Ile
1               5                   10                  15

Ser Thr Cys Glu Trp Lys Met Asn Gly Pro Thr Asn Cys Ser Thr Glu
            20                  25                  30

Leu Arg Leu Leu Tyr Gln Leu Val Phe Leu Leu Ser Glu Ala His Thr
        35                  40                  45

Cys Ile Pro Glu Asn Asn Gly Gly Ala Gly Cys Val Cys His Leu Leu
```

```
            50                  55                  60
Met Asp Asp Val Val Ser Ala Asp Asn Tyr Thr Leu Asp Leu Trp Ala
 65                  70                  75                  80

Gly Gln Gln Leu Leu Trp Lys Gly Ser Phe Lys Pro Ser Glu His Val
                 85                  90                  95

Lys Pro Arg Ala Pro Gly Asn Leu Thr Val His Thr Asn Val Ser Asp
            100                 105                 110

Thr Leu Leu Leu Thr Trp Ser Asn Pro Tyr Pro Pro Asp Asn Tyr Leu
        115                 120                 125

Tyr Asn His Leu Thr Tyr Ala Val Asn Ile Trp Ser Glu Asn Asp Pro
    130                 135                 140

Ala Asp Phe Arg Ile Tyr Asn Val Thr Tyr Leu Glu Pro Ser Leu Arg
145                 150                 155                 160

Ile Ala Ala Ser Thr Leu Lys Ser Gly Ile Ser Tyr Arg Ala Arg Val
                165                 170                 175

Arg Ala Trp Ala Gln Cys Tyr Asn Thr Thr Trp Ser Glu Trp Ser Pro
            180                 185                 190

Ser Thr Lys Trp His Asn Ser Tyr Arg Glu Pro Phe Glu Gln His
        195                 200                 205

<210> SEQ ID NO 2
<211> LENGTH: 208
<212> TYPE: PRT
<213> ORGANISM: Mus musculus

<400> SEQUENCE: 2

Ile Lys Val Leu Gly Glu Pro Thr Cys Phe Ser Asp Tyr Ile Arg Thr
  1               5                  10                  15

Ser Thr Cys Glu Trp Phe Leu Asp Ser Ala Val Asp Cys Ser Ser Gln
                 20                  25                  30

Leu Cys Leu His Tyr Arg Leu Met Phe Phe Glu Phe Ser Glu Asn Leu
             35                  40                  45

Thr Cys Ile Pro Arg Asn Ser Ala Ser Thr Val Cys Val Cys His Met
         50                  55                  60

Glu Met Asn Arg Pro Val Gln Ser Asp Arg Tyr Gln Met Glu Leu Trp
 65                  70                  75                  80

Ala Glu His Arg Gln Leu Trp Gln Gly Ser Phe Ser Pro Ser Gly Asn
                 85                  90                  95

Val Lys Pro Leu Ala Pro Asp Asn Leu Thr Leu His Thr Asn Val Ser
            100                 105                 110

Asp Glu Trp Leu Leu Thr Trp Asn Asn Leu Tyr Pro Ser Asn Asn Leu
        115                 120                 125

Leu Tyr Lys Asp Leu Ile Ser Met Val Asn Ile Ser Arg Glu Asp Asn
    130                 135                 140

Pro Ala Glu Phe Ile Val Tyr Asn Val Thr Tyr Lys Glu Pro Arg Leu
145                 150                 155                 160

Ser Phe Pro Ile Asn Ile Leu Met Ser Gly Val Tyr Tyr Thr Ala Arg
                165                 170                 175

Val Arg Val Arg Ser Gln Ile Leu Thr Gly Thr Trp Ser Glu Trp Ser
            180                 185                 190

Pro Ser Ile Thr Trp Tyr Asn His Phe Gln Leu Pro Leu Ile Gln Arg
        195                 200                 205

<210> SEQ ID NO 3
<211> LENGTH: 209
```

<212> TYPE: PRT
<213> ORGANISM: Macaca mulatta

<400> SEQUENCE: 3

```
Gly Asn Met Lys Val Leu Gln Glu Pro Ala Cys Val Ser Asp Tyr Met
1               5                   10                  15

Ser Ile Ser Thr Cys Glu Trp Lys Met Gly Gly Pro Thr Asn Cys Ser
            20                  25                  30

Ala Glu Leu Arg Leu Leu Tyr Gln Leu Val Phe Gln Ser Ser Glu Thr
        35                  40                  45

His Thr Cys Val Pro Glu Asn Asn Gly Gly Val Gly Cys Val Cys His
    50                  55                  60

Leu Leu Met Asp Asp Val Val Ser Met Asp Asn Tyr Thr Leu Asp Leu
65                  70                  75                  80

Trp Ala Gly Gln Gln Leu Leu Trp Lys Gly Ser Phe Lys Pro Ser Glu
                85                  90                  95

His Val Lys Pro Arg Ala Pro Gly Asn Leu Thr Val His Thr Asn Val
            100                 105                 110

Ser Asp Thr Val Leu Leu Thr Trp Ser Asn Pro Tyr Pro Pro Asp Asn
        115                 120                 125

Tyr Leu Tyr Asn Asp Leu Thr Tyr Ala Val Asn Ile Trp Ser Glu Asn
    130                 135                 140

Asp Pro Ala Tyr Ser Arg Ile His Asn Val Thr Tyr Leu Lys Pro Thr
145                 150                 155                 160

Leu Arg Ile Pro Ala Ser Thr Leu Lys Ser Gly Ile Ser Tyr Arg Ala
                165                 170                 175

Arg Val Arg Ala Trp Ala Gln His Tyr Asn Thr Thr Trp Ser Glu Trp
            180                 185                 190

Ser Pro Ser Thr Lys Trp Tyr Asn Ser Tyr Arg Glu Pro Phe Glu Gln
        195                 200                 205

Arg
```

<210> SEQ ID NO 4
<211> LENGTH: 129
<212> TYPE: PRT
<213> ORGANISM: Homo sapiens

<400> SEQUENCE: 4

```
His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser
```

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

His His His His His His
1               5

<210> SEQ ID NO 6
<211> LENGTH: 232
<212> TYPE: PRT
<213> ORGANISM: Homo sapiens

<400> SEQUENCE: 6

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 7
<211> LENGTH: 232
<212> TYPE: PRT
<213> ORGANISM: Mus musculus

<400> SEQUENCE: 7

Pro Arg Gly Pro Thr Ile Lys Pro Cys Pro Pro Cys Lys Cys Pro Ala
1               5                   10                  15

Pro Asn Leu Leu Gly Gly Pro Ser Val Phe Ile Phe Pro Pro Lys Ile

```
                 20                  25                  30
Lys Asp Val Leu Met Ile Ser Leu Ser Pro Ile Val Thr Cys Val Val
             35                  40                  45

Val Asp Val Ser Glu Asp Asp Pro Asp Val Gln Ile Ser Trp Phe Val
 50                  55                  60

Asn Asn Val Glu Val His Thr Ala Gln Thr Gln Thr His Arg Glu Asp
 65                  70                  75                  80

Tyr Asn Ser Thr Leu Arg Val Val Ser Ala Leu Pro Ile Gln His Gln
                 85                  90                  95

Asp Trp Met Ser Gly Lys Glu Phe Lys Cys Lys Val Asn Asn Lys Asp
             100                 105                 110

Leu Pro Ala Pro Ile Glu Arg Thr Ile Ser Lys Pro Lys Gly Ser Val
         115                 120                 125

Arg Ala Pro Gln Val Tyr Val Leu Pro Pro Glu Glu Glu Met Thr
     130                 135                 140

Lys Lys Gln Val Thr Leu Thr Cys Met Val Thr Asp Phe Met Pro Glu
145                 150                 155                 160

Asp Ile Tyr Val Glu Trp Thr Asn Asn Gly Lys Thr Glu Leu Asn Tyr
                 165                 170                 175

Lys Asn Thr Glu Pro Val Leu Asp Ser Asp Gly Ser Tyr Phe Met Tyr
             180                 185                 190

Ser Lys Leu Arg Val Glu Lys Lys Asn Trp Val Glu Arg Asn Ser Tyr
         195                 200                 205

Ser Cys Ser Val Val His Glu Gly Leu His Asn His His Thr Thr Lys
     210                 215                 220

Ser Phe Ser Arg Thr Pro Gly Lys
225                 230

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
     130                 135                 140

Val Val Val Asp Val Ser His Glu Asp Pro Glu Val Lys Phe Asn Trp
145                 150                 155                 160
```

Tyr Val Asp Gly Val Glu Val His Asn Ala Lys Thr Lys Pro Arg Glu
              165                 170                 175

Glu Gln Tyr Asn Ser Thr Tyr Arg Val Val Ser Val Leu Thr Val Leu
          180                 185                 190

His Gln Asp Trp Leu Asn Gly Lys Glu Tyr Lys Cys Lys Val Ser Asn
      195                 200                 205

Lys Ala Leu Pro Ala Pro Ile Glu Lys Thr Ile Ser Lys Ala Lys Gly
  210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
              245                 250                 255

Pro Ser Asp Ile Ala Val Glu Trp Glu Ser Asn Gly Gln Pro Glu Asn
          260                 265                 270

Asn Tyr Lys Thr Thr Pro Pro Val Leu Asp Ser Asp Gly Ser Phe Phe
      275                 280                 285

Leu Tyr Ser Lys Leu Thr Val Asp Lys Ser Arg Trp Gln Gln Gly Asn
  290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
              325                 330

<210> SEQ ID NO 9
<211> LENGTH: 326
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
              20                  25                  30

Phe Pro Glu Pro Val Thr Val Ser Trp Asn Ser Gly Ala Leu Thr Ser
          35                  40                  45

Gly Val His Thr Phe Pro Ala Val Leu Gln Ser Ser Gly Leu Tyr Ser
      50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
              85                  90                  95

Thr Val Glu Arg Lys Cys Cys Val Glu Cys Pro Pro Cys Pro Ala Pro
          100                 105                 110

Pro Val Ala Gly Pro Ser Val Phe Leu Phe Pro Pro Lys Pro Lys Asp
      115                 120                 125

Thr Leu Met Ile Ser Arg Thr Pro Glu Val Thr Cys Val Val Val Asp
  130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
              165                 170                 175

Ser Thr Phe Arg Val Val Ser Val Leu Thr Val Val His Gln Asp Trp
          180                 185                 190

Leu Asn Gly Lys Glu Tyr Lys Cys Lys Val Ser Asn Lys Gly Leu Pro
      195                 200                 205

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                    245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 10
<211> LENGTH: 327
<212> TYPE: PRT
<213> ORGANISM: Homo sapiens

<400> SEQUENCE: 10

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

|   |   |   | 245 |   |   |   | 250 |   |   |   | 255 |   |   |
|---|---|---|---|---|---|---|---|---|---|---|---|---|---|

Ile Ala Val Glu Trp Glu Ser Asn Gly Gln Pro Glu Asn Asn Tyr Lys
        260            265            270

Thr Thr Pro Pro Val Leu Asp Ser Asp Gly Ser Phe Phe Leu Tyr Ser
        275            280            285

Arg Leu Thr Val Asp Lys Ser Arg Trp Gln Glu Gly Asn Val Phe Ser
        290            295            300

Cys Ser Val Met His Glu Ala Leu His Asn His Tyr Thr Gln Lys Ser
305            310            315            320

Leu Ser Leu Ser Leu Gly Lys
        325

<210> SEQ ID NO 11
<211> LENGTH: 324
<212> TYPE: PRT
<213> ORGANISM: Mus musculus

<400> SEQUENCE: 11

Ala Lys Thr Thr Pro Pro Ser Val Tyr Pro Leu Ala Pro Gly Ser Ala
1              5              10            15

Ala Gln Thr Asn Ser Met Val Thr Leu Gly Cys Leu Val Lys Gly Tyr
        20            25            30

Phe Pro Glu Pro Val Thr Val Thr Trp Asn Ser Gly Ser Leu Ser Ser
        35            40            45

Gly Val His Thr Phe Pro Ala Val Leu Glu Ser Asp Leu Tyr Thr Leu
        50            55            60

Ser Ser Ser Val Thr Val Pro Ser Ser Pro Arg Pro Ser Glu Thr Val
65              70            75            80

Thr Cys Asn Val Ala His Pro Ala Ser Ser Thr Lys Val Asp Lys Lys
        85            90            95

Ile Val Pro Arg Asp Cys Gly Cys Lys Pro Cys Ile Cys Thr Val Pro
        100           105           110

Glu Val Ser Ser Val Phe Ile Phe Pro Pro Lys Pro Lys Asp Val Leu
        115           120           125

Thr Ile Thr Leu Thr Pro Lys Val Thr Cys Val Val Asp Ile Ser
        130           135           140

Lys Asp Asp Pro Glu Val Gln Phe Ser Trp Phe Val Asp Val Glu
145            150           155           160

Val His Thr Ala Gln Thr Gln Pro Arg Glu Glu Gln Phe Asn Ser Thr
        165           170           175

Phe Arg Ser Val Ser Glu Leu Pro Ile Met His Gln Asp Trp Leu Asn
        180           185           190

Gly Lys Glu Phe Lys Cys Arg Val Asn Ser Ala Ala Phe Pro Ala Pro
        195           200           205

Ile Glu Lys Thr Ile Ser Lys Thr Lys Gly Arg Pro Lys Ala Pro Gln
        210           215           220

Val Tyr Thr Ile Pro Pro Pro Lys Glu Gln Met Ala Lys Asp Lys Val
225            230           235           240

Ser Leu Thr Cys Met Ile Thr Asp Phe Phe Pro Glu Asp Ile Thr Val
        245           250           255

Glu Trp Gln Trp Asn Gly Gln Pro Ala Glu Asn Tyr Lys Asn Thr Gln
        260           265           270

Pro Ile Met Asn Thr Asn Gly Ser Tyr Phe Val Tyr Ser Lys Leu Asn
        275           280           285

```
Val Gln Lys Ser Asn Trp Glu Ala Gly Asn Thr Phe Thr Cys Ser Val
290                 295                 300

Leu His Glu Gly Leu His Asn His His Thr Glu Lys Ser Leu Ser His
305                 310                 315                 320

Ser Pro Gly Lys

<210> SEQ ID NO 12
<211> LENGTH: 330
<212> TYPE: PRT
<213> ORGANISM: Mus musculus

<400> SEQUENCE: 12

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

<210> SEQ ID NO 13
<211> LENGTH: 107
<212> TYPE: PRT
<213> ORGANISM: Homo sapiens

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 14
<211> LENGTH: 106
<212> TYPE: PRT
<213> ORGANISM: Homo sapiens

<400> SEQUENCE: 14

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 15
<211> LENGTH: 107
<212> TYPE: PRT
<213> ORGANISM: Mus musculus

<400> SEQUENCE: 15

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu

```
                65                  70                  75                  80
Arg His Asn Ser Tyr Thr Cys Glu Ala Thr His Lys Thr Ser Thr Ser
                    85                  90                  95

Pro Ile Val Lys Ser Phe Asn Arg Asn Glu Cys
            100                 105

<210> SEQ ID NO 16
<211> LENGTH: 106
<212> TYPE: PRT
<213> ORGANISM: Mus musculus

<400> SEQUENCE: 16

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 17
<211> LENGTH: 252
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Thr Gly Gly Gly Gly Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Ser Ile Thr Ile Arg Pro Arg Tyr Phe Gly Leu
            100                 105                 110

Asp Phe Trp Gly Gln Gly Thr Thr Val Thr Val Ser Ser Gly Gly Gly
        115                 120                 125

Gly Ser Gly Gly Gly Gly Ser Gly Gly Gly Gly Ser Asp Ile Val Met
    130                 135                 140

Thr Gln Ser Pro Leu Ser Leu Pro Val Thr Pro Gly Glu Pro Ala Ser
145                 150                 155                 160

Ile Ser Cys Arg Ser Ser Arg Ser Val Leu Tyr Gly Asn Gly Tyr Asn
                165                 170                 175
```

Tyr Leu Asp Trp Tyr Leu Gln Lys Ser Gly Gln Ser Pro Gln Leu Leu
            180                 185                 190

Ile Tyr Leu Gly Thr Asn Val Ala Ala Gly Val Pro Asp Arg Phe Ser
            195                 200                 205

Gly Ser Gly Ser Gly Thr Asp Phe Thr Leu Lys Ile Ser Arg Val Glu
210                 215                 220

Ala Glu Asp Val Gly Phe Tyr Tyr Cys Met Gln Ser Leu Arg Thr Pro
225                 230                 235                 240

Tyr Thr Phe Gly Gln Gly Thr Lys Leu Glu Ile Lys
                245                 250

<210> SEQ ID NO 18
<211> LENGTH: 125
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Thr Gly Gly Gly Gly Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Arg Ile Ser Ile Thr Ile Arg Pro Arg Tyr Phe Gly Leu
            100                 105                 110

Asp Phe Trp Gly Gln Gly Thr Thr Val Thr Val Ser Ser
        115                 120                 125

<210> SEQ ID NO 19
<211> LENGTH: 112
<212> TYPE: PRT
<213> ORGANISM: Artificial Sequence
<220> FEATURE:
<223> OTHER INFORMATION: Synthetic

<400> SEQUENCE: 19

Asp Ile Val Met Thr Gln Ser Pro Leu Ser Leu Pro Val Thr Pro Gly
1               5                   10                  15

Glu Pro Ala Ser Ile Ser Cys Arg Ser Ser Arg Ser Val Leu Tyr Gly
            20                  25                  30

Asn Gly Tyr Asn Tyr Leu Asp Trp Tyr Leu Gln Lys Ser Gly Gln Ser
        35                  40                  45

Pro Gln Leu Leu Ile Tyr Leu Gly Thr Asn Val Ala Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Leu Arg Thr Pro Tyr Thr Phe Gly Gln Gly Thr Lys Leu Glu Ile Lys

<210> SEQ ID NO 20
<211> LENGTH: 243
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Arg Trp Val Arg Gln Ala Pro Gly Lys Gly Leu Glu Trp Val
        35                  40                  45

Ser Phe Ile Ser Ala Ser Gly Ser Thr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Pro Thr Ala Pro Arg Ser Ser Ala Leu Asp Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Asp Arg Val Thr Ile Thr Cys Arg
145                 150                 155                 160

Ala Ser Gln Gly Val Asn Asn Tyr Leu Asn Trp Tyr Gln Gln Lys Pro
                165                 170                 175

Gly Lys Ala Pro Lys Leu Leu Ile Tyr Gly Ala Ser Ser Arg Ala Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Arg Leu Ser Val Pro Leu Thr Phe Gly Gln Gly Thr Lys Val
225                 230                 235                 240

Glu Ile Lys

<210> SEQ ID NO 21
<211> LENGTH: 121
<212> TYPE: PRT
<213> ORGANISM: Artificial Sequence
<220> FEATURE:
<223> OTHER INFORMATION: Synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ser Met Arg Trp Val Arg Gln Ala Pro Gly Lys Gly Leu Glu Trp Val
        35                  40                  45

Ser Phe Ile Ser Ala Ser Gly Ser Thr Lys Tyr Tyr Ala Asp Ser Val

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Lys Pro Thr Ala Pro Arg Ser Ser Ala Leu Asp Tyr Trp Gly
                100                 105                 110

Gln Gly Thr Leu Val Thr Val Ser Ser
            115                 120

<210> SEQ ID NO 22
<211> LENGTH: 107
<212> TYPE: PRT
<213> ORGANISM: Artificial Sequence
<220> FEATURE:
<223> OTHER INFORMATION: Synthetic

<400> SEQUENCE: 22

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Val Asn Asn Tyr
             20                  25                  30

Leu Asn Trp Tyr Gln Gln Lys Pro Gly Lys Ala Pro Lys Leu Leu Ile
             35                  40                  45

Tyr Gly Ala Ser Ser Arg Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Arg Leu Ser Val Pro Leu
                 85                  90                  95

Thr Phe Gly Gln Gly Thr Lys Val Glu Ile Lys
            100                 105

<210> SEQ ID NO 23
<211> LENGTH: 246
<212> TYPE: PRT
<213> ORGANISM: Artificial Sequence
<220> FEATURE:
<223> OTHER INFORMATION: Synthetic

<400> SEQUENCE: 23

Gln Val Gln Leu Gln Gln Ser Gly Pro Gly Leu Val Lys Pro Ser Gln
  1               5                  10                  15

Thr Leu Ser Leu Thr Cys Ala Ile Ser Gly Asp Ser Val Ser Ser Asn
             20                  25                  30

Asn Asp Ala Trp Asn Trp Ile Arg Gln Ser Pro Ser Arg Gly Leu Glu
             35                  40                  45

Trp Leu Gly Arg Thr Tyr Tyr Arg Ser Lys Trp Tyr Asn Asp Tyr Ala
     50                  55                  60

Val Ser Leu Lys Gly Arg Ile Thr Ile Asn Pro Asp Thr Ser Lys Asn
 65                  70                  75                  80

Gln Phe Ser Leu His Leu Asn Ser Val Thr Pro Glu Asp Thr Ala Val
                 85                  90                  95

Tyr Tyr Cys Ala Lys Arg Asp Ser Ser Val Gly Val Gly Ala Met Asp
            100                 105                 110

Val Trp Ser Gln Gly Thr Thr Val Thr Val Ser Ser Gly Gly Gly Gly
            115                 120                 125
```

```
Ser Gly Gly Gly Ser Gly Gly Gly Ser Val Ile Trp Met Thr
    130             135             140

Gln Ser Pro Ser Ser Leu Ser Ala Ser Val Gly Asp Arg Val Thr Ile
145             150                 155                 160

Thr Cys Arg Ser Ser Gln Tyr Ile Gly Lys Tyr Leu Asn Trp Tyr Gln
                165                 170                 175

Tyr Lys Lys Gly Gln Val Pro Lys Leu Leu Ile Tyr Ala Ala Ser Ser
            180                 185                 190

Leu Arg Ser Gly Val Pro Ser Arg Phe Ser Gly Arg Gly Ser Ala Thr
        195                 200                 205

Glu Phe Thr Leu Thr Ile Ser Asn Leu Gln Arg Glu Asp Phe Ala Thr
    210                 215                 220

Tyr Tyr Cys Gln Lys Tyr Asn Ala Val Pro Leu Thr Phe Gly Gln Gly
225             230                 235                 240

Thr Lys Leu Glu Ile Lys
            245
```

<210> SEQ ID NO 24
<211> LENGTH: 124
<212> TYPE: PRT
<213> ORGANISM: Artificial Sequence
<220> FEATURE:
<223> OTHER INFORMATION: Synthetic

<400> SEQUENCE: 24

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Asn Asp Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Leu Lys Gly Arg Ile Thr Ile Asn Pro Asp Thr Ser Lys Asn
65                  70                  75                  80

Gln Phe Ser Leu His Leu Asn Ser Val Thr Pro Glu Asp Thr Ala Val
                85                  90                  95

Tyr Tyr Cys Ala Lys Arg Asp Ser Ser Val Gly Val Gly Ala Met Asp
            100                 105                 110

Val Trp Ser Gln Gly Thr Thr Val Thr Val Ser Ser
        115                 120
```

<210> SEQ ID NO 25
<211> LENGTH: 107
<212> TYPE: PRT
<213> ORGANISM: Artificial Sequence
<220> FEATURE:
<223> OTHER INFORMATION: Synthetic

<400> SEQUENCE: 25

```
Val Ile Trp Met Thr Gln Ser Pro Ser Leu Ser Ala Ser Val Gly
1               5                   10                  15

Asp Arg Val Thr Ile Thr Cys Arg Ser Ser Gln Tyr Ile Gly Lys Tyr
            20                  25                  30

Leu Asn Trp Tyr Gln Tyr Lys Lys Gly Gln Val Pro Lys Leu Leu Ile
        35                  40                  45

Tyr Ala Ala Ser Ser Leu Arg Ser Gly Val Pro Ser Arg Phe Ser Gly
    50                  55                  60
```

-continued

Arg Gly Ser Ala Thr Glu Phe Thr Leu Thr Ile Ser Asn Leu Gln Arg
65                  70                  75                  80

Glu Asp Phe Ala Thr Tyr Tyr Cys Gln Lys Tyr Asn Ala Val Pro Leu
                85                  90                  95

Thr Phe Gly Gln Gly Thr Lys Leu Glu Ile Lys
            100                 105

<210> SEQ ID NO 26
<211> LENGTH: 112
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu Tyr Ser
                20                  25                  30

Ile Gly Tyr Asn Tyr Leu Asp Trp Tyr Leu Gln Lys Ser Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Phe Lys Ala Pro Tyr Thr Phe Gly Gln Gly Thr Lys Leu Glu Ile Lys
            100                 105                 110

<210> SEQ ID NO 27
<211> LENGTH: 112
<212> TYPE: PRT
<213> ORGANISM: Artificial Sequence
<220> FEATURE:
<223> OTHER INFORMATION: Synthetic

<400> SEQUENCE: 27

Asp Ile Val Met Thr Gln Ser Pro Leu Ser Leu Pro Val Thr Pro Gly
1               5                   10                  15

Glu Pro Ala Ser Ile Ser Cys Arg Ser Ser Arg Asn Val Ile Tyr Gly
                20                  25                  30

Asn Gly Tyr Asn Tyr Leu Asp Trp Tyr Leu Gln Lys Ser Gly Gln Ser
            35                  40                  45

Pro Gln Leu Leu Ile Tyr Leu Gly Asn Asn Val Ala Ala Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Leu Gln Ala Pro Tyr Thr Phe Gly Gln Gly Thr Lys Leu Glu Ile Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: Synthetic

```
<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Val Val Tyr Gly
            20                  25                  30

Asn Gly Tyr Asn Tyr Leu Asp Trp Tyr Leu Gln Lys Ser Gly Gln Ser
        35                  40                  45

Pro Gln Leu Leu Ile Tyr Leu Gly Thr Asn Val Ala Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Leu Gln Ala Pro Tyr Thr Phe Gly Gln Gly Thr Lys Leu Glu Ile Lys
            100                 105                 110

<210> SEQ ID NO 29
<211> LENGTH: 112
<212> TYPE: PRT
<213> ORGANISM: Artificial Sequence
<220> FEATURE:
<223> OTHER INFORMATION: Synthetic

<400> SEQUENCE: 29

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Asn Val Val Tyr Gly
            20                  25                  30

Asn Gly Tyr Asn Tyr Leu Asp Trp Tyr Leu Gln Lys Ser Gly Gln Ser
        35                  40                  45

Pro Gln Leu Leu Ile Tyr Leu Gly Asn Asn Val Ala Ala Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Phe Tyr Tyr Cys Met Gln Ser
                85                  90                  95

Leu Lys Ala Pro Tyr Thr Phe Gly Gln Gly Thr Lys Leu Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Synthetic

<400> SEQUENCE: 30

Asp Ile Val Met Thr Gln Ser Pro Leu Ser Leu Pro Val Thr Pro Gly
1               5                   10                  15

Glu Pro Ala Ser Ile Ser Cys Arg Ser Ser His Asn Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Tyr Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr His Cys Met Gln Ala
                85                  90                  95

Leu Gln Ser Pro Tyr Thr Phe Gly Gln Gly Thr Lys Val Asp Ile Lys
            100                 105                 110
```

<210> SEQ ID NO 31
<211> LENGTH: 112
<212> TYPE: PRT
<213> ORGANISM: Artificial Sequence
<220> FEATURE:
<223> OTHER INFORMATION: Synthetic

<400> SEQUENCE: 31

```
Asp Ile Val Met Thr Gln Ser Pro Leu Ser Leu Pro Val Thr Ala Gly
1               5                   10                  15

Ala Pro Ala Ser Ile Ser Cys Arg Ser Ser Gln Ser Leu Leu Tyr Ser
                20                  25                  30

Asn Gly Tyr Asn Tyr Leu Asp Trp Tyr Met Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Thr Pro Tyr Ala Phe Gly Gln Gly Thr Lys Val Glu Ile Lys
            100                 105                 110
```

<210> SEQ ID NO 32
<211> LENGTH: 122
<212> TYPE: PRT
<213> ORGANISM: Homo sapiens

<400> SEQUENCE: 32

```
Leu Thr Cys Leu Gly Gly Phe Ala Ser Pro Gly Pro Val Pro Pro Ser
1               5                   10                  15

Thr Ala Leu Arg Glu Leu Ile Glu Glu Leu Val Asn Ile Thr Gln Asn
                20                  25                  30

Gln Lys Ala Pro Leu Cys Asn Gly Ser Met Val Trp Ser Ile Asn Leu
            35                  40                  45

Thr Ala Gly Met Tyr Cys Ala Ala Leu Glu Ser Leu Ile Asn Val Ser
        50                  55                  60

Gly Cys Ser Ala Ile Glu Lys Thr Gln Arg Met Leu Ser Gly Phe Cys
65                  70                  75                  80

Pro His Lys Val Ser Ala Gly Gln Phe Ser Ser Leu His Val Arg Asp
                85                  90                  95

Thr Lys Ile Glu Val Ala Gln Phe Val Lys Asp Leu Leu Leu His Leu
            100                 105                 110

Lys Lys Leu Phe Arg Glu Gly Arg Phe Asn
        115                 120
```

<210> SEQ ID NO 33
<211> LENGTH: 10
<212> TYPE: PRT
<213> ORGANISM: Artificial Sequence
<220> FEATURE:
<223> OTHER INFORMATION: Synthetic

<400> SEQUENCE: 33

```
Gly Phe Thr Phe Ser Ser Tyr Ala Met Ser
1               5                   10
```

<210> SEQ ID NO 34
<211> LENGTH: 17
<212> TYPE: PRT
<213> ORGANISM: Artificial Sequence
<220> FEATURE:
<223> OTHER INFORMATION: Synthetic

<400> SEQUENCE: 34

```
Ser Ile Thr Gly Gly Gly Gly Ile Tyr Tyr Ala Asp Ser Val Lys
1               5                   10                  15

Gly
```

<210> SEQ ID NO 35
<211> LENGTH: 16
<212> TYPE: PRT
<213> ORGANISM: Artificial Sequence
<220> FEATURE:
<223> OTHER INFORMATION: Synthetic

<400> SEQUENCE: 35

```
Asp Arg Ile Ser Ile Thr Ile Arg Pro Arg Tyr Phe Gly Leu Asp Phe
1               5                   10                  15
```

<210> SEQ ID NO 36
<211> LENGTH: 16
<212> TYPE: PRT
<213> ORGANISM: Artificial Sequence
<220> FEATURE:
<223> OTHER INFORMATION: Synthetic

<400> SEQUENCE: 36

```
Arg Ser Ser Gln Ser Leu Leu Tyr Ser Ile Gly Tyr Asn Tyr Leu Asp
1               5                   10                  15
```

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

```
Leu Gly Ser Asn Arg Ala Ser
1               5
```

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

```
Met Gln Ser Phe Lys Ala Pro Tyr Thr
1               5
```

<210> SEQ ID NO 39
<211> LENGTH: 16
<212> TYPE: PRT
<213> ORGANISM: Artificial Sequence
<220> FEATURE:
<223> OTHER INFORMATION: Synthetic

```
<400> SEQUENCE: 39

Arg Ser Ser Arg Asn Val Ile Tyr Gly Asn Gly Tyr Asn Tyr Leu Asp
1               5                   10                  15

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Leu Gly Asn Asn Val Ala Ala
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Met Gln Ser Leu Gln Ala Pro Tyr Thr
1               5

<210> SEQ ID NO 42
<211> LENGTH: 15
<212> TYPE: PRT
<213> ORGANISM: Artificial Sequence
<220> FEATURE:
<223> OTHER INFORMATION: Synthetic

<400> SEQUENCE: 42

Arg Ser Ser Gln Asn Val Tyr Gly Asn Gly Tyr Asn Tyr Leu Asp
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: Synthetic

<400> SEQUENCE: 43

Leu Gly Thr Asn Val Ala Ala
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Met Gln Ser Leu Lys Ala Pro Tyr Thr
1               5

<210> SEQ ID NO 45
<211> LENGTH: 16
<212> TYPE: PRT
<213> ORGANISM: Artificial Sequence
<220> FEATURE:
<223> OTHER INFORMATION: Synthetic

<400> SEQUENCE: 45
```

Arg Ser Ser His Asn Leu Leu Tyr Ser Asn Gly Tyr Asn Tyr Leu Asp
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Synthetic

<400> SEQUENCE: 46

Leu Gly Ser Asn Arg Ala Tyr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Met Gln Ala Leu Gln Ser Pro Tyr Thr
1               5

<210> SEQ ID NO 48
<211> LENGTH: 16
<212> TYPE: PRT
<213> ORGANISM: Artificial Sequence
<220> FEATURE:
<223> OTHER INFORMATION: Synthetic

<400> SEQUENCE: 48

Arg Ser Ser Gln Ser Leu Leu Tyr Ser Asn Gly Tyr Asn Tyr Leu Asp
1               5                   10                  15

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Met Gln Ala Leu Glu Thr Pro Tyr Ala
1               5

<210> SEQ ID NO 50
<211> LENGTH: 32
<212> TYPE: DNA
<213> ORGANISM: Artificial Sequence
<220> FEATURE:
<223> OTHER INFORMATION: Synthetic

<400> SEQUENCE: 50
atgccatggc ggacatcgtg atgacacaga gc                              32

<210> SEQ ID NO 51
<211> LENGTH: 65
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(40)
<223> OTHER INFORMATION: n is a, c, g, or t

```
<400> SEQUENCE: 51
taccagtcca ggtagttgta gccawtasyg kwgabgaban tkyggctgct tctacagctg      60
atgct                                                                 65

<210> SEQ ID NO 52
<211> LENGTH: 23
<212> TYPE: DNA
<213> ORGANISM: Artificial Sequence
<220> FEATURE:
<223> OTHER INFORMATION: Synthetic

<400> SEQUENCE: 52
ggctacaact acctggactg gta                                             23

<210> SEQ ID NO 53
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (21)..(21)
<223> OTHER INFORMATION: n is a, c, g, or t

<400> SEQUENCE: 53
atctatcggg cacgccgkmg ncamcabtgk wavccaggta gatcagcagc tgagg           55

<210> SEQ ID NO 54
<211> LENGTH: 16
<212> TYPE: DNA
<213> ORGANISM: Artificial Sequence
<220> FEATURE:
<223> OTHER INFORMATION: Synthetic

<400> SEQUENCE: 54
ggcgtgcccg atagat                                                     16

<210> SEQ ID NO 55
<211> LENGTH: 54
<212> TYPE: DNA
<213> ORGANISM: Artificial Sequence
<220> FEATURE:
<223> OTHER INFORMATION: Synthetic

<400> SEQUENCE: 55
cctggccaaa ggtgtaagga ghtykkaagg mctgcataca gtagtagaag ccca            54

<210> SEQ ID NO 56
<211> LENGTH: 45
<212> TYPE: DNA
<213> ORGANISM: Artificial Sequence
<220> FEATURE:
<223> OTHER INFORMATION: Synthetic

<400> SEQUENCE: 56
cgtacgcttg atttccagct tggtgccctg gccaaaggtg taagg                      45
```